US005686284A

United States Patent [19]
Fujii et al.

[11] Patent Number: 5,686,284
[45] Date of Patent: Nov. 11, 1997

[54] ALCOHOL ACETYLTRANSFERASE GENES AND USE THEREOF

[75] Inventors: Toshio Fujii; Akihiro Iwamatsu; Hiroyuki Yoshimoto, all of Tokyo-to; Toshitaka Minetoki, Nishinomiya; Takayuki Bogaki, Nishinomiya; Naoshi Nagasawa, Nishinomiya, all of Japan

[73] Assignee: Kirin Beer Kabushiki Kaisha, Tokyo-to, Japan

[21] Appl. No.: 461,621

[22] Filed: Jun. 5, 1995

Related U.S. Application Data

[62] Division of Ser. No. 77,939, Jun. 18, 1993, Pat. No. 5,521,088.

[30] Foreign Application Priority Data

Jun. 18, 1992 [JP] Japan .................................. 4-184328
Feb. 26, 1993 [JP] Japan .................................. 5-062997

[51] Int. Cl.$^6$ .......................... C12N 9/10; C12N 9/00; C07H 21/04
[52] U.S. Cl. ........................ 435/193; 536/23.2; 435/320.1
[58] Field of Search .......................... 435/193, 320.1; 536/23.2

[56] References Cited

U.S. PATENT DOCUMENTS 4,394,443  7/1983  Weissman ..................................... 435/6

FOREIGN PATENT DOCUMENTS 9-106636  5/1991  WIPO .

OTHER PUBLICATIONS

Yoshioka et al., "Agric. Biol. Chem.", 45(10):2183–2190 (1981).
Akita et al., "Agric. Biol. Chem.", 54(6):1485–1490 (1990).
Malcorps et al., "Eur. J. Biochem.", 210:1015–1022 (1992).

Mauricio et al., "J. Agric. Food Chem.", 41:2086–2091 (1993).

Hewick et al., "J. Biol. Chem.", 256(15):7990–9777 (1981).

Hunkapillier et al., "Science", 226:304–311 (1984).

Chemical Abstracts No. 93765t, vol. 113, No. 11, Columbus, Ohio, US: Akita, Osamu, Suzuki, Syuzi Obata, Takaji, Hara, Shodo, "Purification and some properties of alcohol acetyltransferase from sake".

Biosis Previews Database, Philadelphia, US, Abstract No. 95066783, Malcorps P., Dufour, J–P., "Short–Chain and Medium–Chain Aliphatic Ester Synthesis in Sacchromyces–Cerevisiae." (1992).

Biosis Previews Database, Philadelphia, US, Abstract No. 88025463, Yanaguichi T., Kiyokawa Y., Wakai Y., "Isolation of Sake–Yeast Strains Accumulating Large Amounts of Isoamyl Acetate." (1989).

Patent Abstracts of Japan, vol. 014, No. 192 (C–0711) (Apr. 19, 1990).

Malcorps P. et al.—"Short–chain & Medium–Chain aliphatic ester Synthesis in S. cerevisiae", Eur. J. Biochem. 210(3):1015–1022 (1992).

*Primary Examiner*—Robert A. Wax
*Assistant Examiner*—Einar Stole
*Attorney, Agent, or Firm*—Foley & Lardner

[57] ABSTRACT

This invention disclosed herein provides an alcohol acetyl transferase ("AATase"), an AATase encoding gene and a yeast having an improved ester producing ability due to transformation with the AATase encoding gene. This invention also provides a process for producing an alcoholic beverage having an enriched ester flavor using the transformed yeast.

5 Claims, 32 Drawing Sheets

FIG. 1(a)

```
  1  AG CGT GTG AGG ACT ACT CAT TGG CTT GCG ATT TAC GGT TTT TAT ATT                    47

48  TTT TGC CGC ACA TCA TTT TTT GGC CTG GTA TTG TCA TCG CGT TGA GCG                    95

96  GAC TCT GAA TAT AAT CCT ATT GTT TTT TAT GGA TCT CTG GAA GCG TCT                   143

144  TTT TGA AGC CAA CCC AAC AAA AAT TCG AGA CAA GAA AAT AAA AAA CGG                   191
                                                                  A
                                                                  ↓
192  CAC TTC ATC AGT ATC ACA AAT ACC ATC AAT TTA TCA GCT CTC ATG AAT                   239
                                                                 Met Asn                 2

240  GAA ATC GAT GAG AAA AAT CAG GCC CCC GTG CAA CAA GAA TGC CTG AAA                   287
     Glu Ile Asp Glu Lys Asn Gln Ala Pro Val Gln Gln Glu Cys Leu Lys                    18
      3

288  GAG ATG ATT CAG AAT GGG CAT GCT CGG CGT ATG GGA TCT GTT GAA GAT                   335
     Glu Met Ile Gln Asn Gly His Ala Arg Arg Met Gly Ser Val Glu Asp                    34
     19
```

FIG. 1(b)

```
336 CTG TAT GTT GCT CTC AAC AGA CAA AAC TTA TAT CGG AAC TTC TGC ACA 383
 35 Leu Tyr Val Ala Leu Asn Arg Gln Asn Leu Tyr Arg Asn Phe Cys Thr  50

384 TAT GGA GAA TTG AGT GAT TAC TGT ACT AGG GAT CAG CTC ACA TTA GCT 431
 51 Tyr Gly Glu Leu Ser Asp Tyr Cys Thr Arg Asp Gln Leu Thr Leu Ala  66

432 TTG AGG GAA ATC TGC CTG AAA AAT CCA ACT CTT TTA CAT ATT GTT CTA 479
 67 Leu Arg Glu Ile Cys Leu Lys Asn Pro Thr Leu Leu His Ile Val Leu  82

480 CCA ATA AGA TGG CCA AAT CAT GAA AAT TAT TAT CGC AGT TCC GAA TAC 527
 83 Pro Ile Arg Trp Pro Asn His Glu Asn Tyr Tyr Arg Ser Ser Glu Tyr  98

528 TAT TCA CGG CCA CAT CCA GTG CAT GAT TAT ATT TCA GTA TTA CAG GAA 575
 99 Tyr Ser Arg Pro His Pro Val His Asp Tyr Ile Ser Val Leu Gln Glu 114

576 TTG AAA CTG AGT GGT GTT CTC AAT GAA CAA CCT GAG TAC AGT GCA 623
115 Leu Lys Leu Ser Gly Val Leu Asn Glu Gln Pro Glu Tyr Ser Ala 130

624 GTA ATG AAG CAA ATA TTA GAA GAA TTC AAA AAT AGT AAG GGT TCC TAT 671
131 Val Met Lys Gln Ile Leu Glu Glu Phe Lys Asn Ser Lys Gly Ser Tyr 146
```

FIG. 1(c)

```
672  ACT GCA AAA ATT TTT AAA CTT ACT ACC ACT TTG ACT ATT CCT TAC TTT  719
147  Thr Ala Lys Ile Phe Lys Leu Thr Thr Thr Leu Thr Ile Pro Tyr Phe  162

720  GGA CCA ACA GGA CCG AGT TGG CGG CTA ATT TGT CTT CCA GAA GAG CAC  767
163  Gly Pro Thr Gly Pro Ser Trp Arg Leu Ile Cys Leu Pro Glu Glu His  178

768  ACA GAA AAG TGG AAA AAA TTT ATC TTT GTA TCT AAT CAT TGC ATG TCT  815
179  Thr Glu Lys Trp Lys Lys Phe Ile Phe Val Ser Asn His Cys Met Ser  194

816  GAT GGT CGG TCT TCG ATC CAC TTT TTT CAT GAT TTA AGA GAC GAA TTA  863
195  Asp Gly Arg Ser Ser Ile His Phe Phe His Asp Leu Arg Asp Glu Leu  210

864  AAT AAT ATT AAA ACT CCA CCA AAA TTA GAT TAC ATT TTC AAG TAC  911
211  Asn Asn Ile Lys Thr Pro Pro Lys Leu Asp Tyr Ile Phe Lys Tyr  226

912  GAG GAG GAT TAC CAA TTG TTG AGG AAA CTT CCA GAA CCG ATC GAA AAG  959
227  Glu Glu Asp Tyr Gln Leu Leu Arg Lys Leu Pro Glu Pro Ile Glu Lys  242

960  GTG ATA GAC TTT AGA CCA CCG TAC TTG TTT ATT CCG AAG TCA CTT CTT  1007
243  Val Ile Asp Phe Arg Pro Pro Tyr Leu Phe Ile Pro Lys Ser Leu Leu  258
```

FIG. 1(d)

```
1008 TCG GGT TTC ATC TAC AAT CAT TTG AGA TTT TCT TCA AAA GGT GTC TGT  1055
 259 Ser Gly Phe Ile Tyr Asn His Leu Arg Phe Ser Ser Lys Gly Val Cys   274

1056 ATG AGA ATG GAT GAT GTG GAA AAA ACC GAT GTT GTC ACC GAG ATC       1103
 275 Met Arg Met Asp Asp Val Glu Lys Thr Asp Val Val Thr Glu Ile       290

1104 ATC AAT ATT TCA CCA ACA GAA TTT CAA GCG ATT AAA GCA AAT ATT AAA   1151
 291 Ile Asn Ile Ser Pro Thr Glu Phe Gln Ala Ile Lys Ala Asn Ile Lys   306

1152 TCA AAT ATC CAA GGT AAG TGT ACT ATC ACT CCG TTT TTA CAT GTT TGT   1199
 307 Ser Asn Ile Gln Gly Lys Cys Thr Ile Thr Pro Phe Leu His Val Cys   322

1200 TGG TTT GTA TCT CTT CAT AAA TGG GGT AAA TTT TTC AAA CCA TTG AAC   1247
 323 Trp Phe Val Ser Leu His Lys Trp Gly Lys Phe Phe Lys Pro Leu Asn   338

1248 TTC GAA TGG CTT ACG GAT ATT TTT ATC CCC GCA GAT TGC CGC TCA CAA   1295
 339 Phe Glu Trp Leu Thr Asp Ile Phe Ile Pro Ala Asp Cys Arg Ser Gln   354
```

FIG. 1(e)

| | | | | | | | | | | | | | | | | |
|---|---|---|---|---|---|---|---|---|---|---|---|---|---|---|---|---|
| 1296 | CTA | CCA | GAT | GAT | GAA | ATG | AGA | CAG | ATG | TAC | AGA | TAT | GGC | GCT | AAC | 1343 |
| 355 | Leu | Pro | Asp | Asp | Glu | Met | Arg | Gln | Met | Tyr | Arg | Tyr | Gly | Ala | Asn | 370 |
| 1344 | GTT | GGA | TTT | ATT | GAC | TTC | ACC | CCA | TGG | ATA | AGC | GAA | TTT | GAC | ATG | AAT | 1391 |
| 371 | Val | Gly | Phe | Ile | Asp | Phe | Thr | Pro | Trp | Ile | Ser | Glu | Phe | Asp | Met | Asn | 386 |
| 1392 | GAT | AAC | AAA | GAA | AAA | TTT | TGG | CCA | CTT | ATT | GAG | CAC | TAC | CAT | GAA | GTA | 1439 |
| 387 | Asp | Asn | Lys | Glu | Lys | Phe | Trp | Pro | Leu | Ile | Glu | His | Tyr | His | Glu | Val | 402 |
| 1440 | ATT | TCG | GAA | GCT | TTA | AGA | AAT | AAA | AAG | CAC | CTC | CAT | GGC | TTA | GGG | TTC | 1487 |
| 403 | Ile | Ser | Glu | Ala | Leu | Arg | Asn | Lys | Lys | His | Leu | His | Gly | Leu | Gly | Phe | 418 |
| 1488 | AAT | ATA | CAA | GGC | TTC | GTT | CAA | AAA | TAT | GTG | AAT | ATT | GAC | AAG | GTA | ATG | 1535 |
| 419 | Asn | Ile | Gln | Gly | Phe | Val | Gln | Lys | Tyr | Val | Asn | Ile | Asp | Lys | Val | Met | 434 |
| 1536 | TGC | GAT | CGT | GCC | ATC | GGG | AAA | AGA | CGC | GGA | GGT | ACA | TTG | TTA | AGC | AAT | 1583 |
| 435 | Cys | Asp | Arg | Ala | Ile | Gly | Lys | Arg | Arg | Gly | Gly | Thr | Leu | Leu | Ser | Asn | 450 |
| 1584 | GTA | GGT | CTG | TTT | AAT | CAG | TTA | GAG | GAG | CCC | GAT | GCC | AAA | TAT | TCT | ATA | 1631 |
| 451 | Val | Gly | Leu | Phe | Asn | Gln | Leu | Glu | Glu | Pro | Asp | Ala | Lys | Tyr | Ser | Ile | 466 |

FIG. 1(f)

```
1632  TGC GAT TTG GCA TTT GGC CAA TTT CAA GGA TCC TGG CAC CAA GCA TTT  1679
 467  Cys Asp Leu Ala Phe Gly Gln Phe Gln Gly Ser Trp His Gln Ala Phe   482

1680  TCC TTG GGT GTT TGT TCG ACT AAT GTA AAG GGG ATG AAT ATT GTT GTT  1727
 483  Ser Leu Gly Val Cys Ser Thr Asn Val Lys Gly Met Asn Ile Val Val   498

1728  GCT TCA ACA AAA AAT GTT GTT GGT AGC CAA GAA TCT CTC GAA GAG CTT  1775
 499  Ala Ser Thr Lys Asn Val Val Gly Ser Gln Glu Ser Leu Glu Glu Leu   514
                                                   B→
1776  TGC TCC ATT TAT AAA GCT CTC CTT TTA GGC CCT TAG ATC TCA CAT GAT  1823
 515  Cys Ser Ile Tyr Lys Ala Leu Leu Leu Gly Pro ***

1824  GCT TGA CTG ATA TTA TTC GAC AAT ATG ATT ATG TCG TGT AAA TAA CCC  1871

1872  ACT TTC ATG TTG TCA CTC CCT CGG CTT TGG TTG GTT AAA GGG ACT TAT  1919

1920  TGG T
```

FIG. 2(a)

```
  1  GTA GCT TCA TTT GTT GGC ACA GGA CTA TTC CAC CCT TAG AAT TGA CTT   48
 49  TTT GGA CAT TGA GCT AAG GTT CAA TGC ACT CGA TGG TCT TCT CAC TTC   96
 97  CGA ATA TAT AGA TCT AGC GTG TGA GGA CTA CTC ATT GGC TTG CGA TTT  144
145  ACG GTT TTT ATA TTT GCC GCA CAT CAT TTT TTG GCC TGG TAT TGT      192
193  CAT CGC GGT TGA GCG GAC TCT GAA TAT AAT CCT ATT GTT TTT TAT GGA  240
241  TCT CTG GAA GCG TCT TTT TGA AGC CAA CCC AAC AAA AAT TCG AGA CAA  288
289  GAA AAT AAA AAA CGG CAC TTC ATC AGT ATC ACA AAT ACC ATC AAT TTA  336
```

FIG. 2(b)

```
                  A
                  ↓
337  TCA GCT CTC ATG AAT GAA ATC GAT GAG AAA AAT CAG GCC CCC GTG CAA  384
                 Met Asn Glu Ile Asp Glu Lys Asn Gln Ala Pro Val Gln   13

385  CAA GAA TGC CTG AAA GAG ATG ATT CAG AAT GGG CAT GCT CGG CGT ATG  432
     Gln Glu Cys Leu Lys Glu Met Ile Gln Asn Gly His Ala Arg Arg Met   29

433  GGA TCT GTT GAA GAT CTG TAT GTT GCT CTC AAC AGA CAA AAC TTA TAT  480
     Gly Ser Val Glu Asp Leu Tyr Val Ala Leu Asn Arg Gln Asn Leu Tyr   45

481  CGA AAC TTC TGC ACA TAT GGA GAA TTG AGT GAT TAC TGT ACT AGG GAT  528
     Arg Asn Phe Cys Thr Tyr Gly Glu Leu Ser Asp Tyr Cys Thr Arg Asp   61

529  CAG CTC ACA TTA GCT TTG AGG GAA ATC TGC CTG AAA AAT CCA ACT CTT  576
     Gln Leu Thr Leu Ala Leu Arg Glu Ile Cys Leu Lys Asn Pro Thr Leu   77

577  TTA CAT ATT GTT CTA CCA ACA AGA TGG CCA AAT CAT GAA AAT TAT TAT  624
     Leu His Ile Val Leu Pro Thr Arg Trp Pro Asn His Glu Asn Tyr Tyr   93

625  CGC AGT TCC GAA TAC TAT TCA CGG CCA CAT CCA GTG CAT GAT TAT ATC  672
     Arg Ser Ser Glu Tyr Tyr Ser Arg Pro His Pro Val His Asp Tyr Ile  109
```

FIG. 2(c)

```
673  TCA GTA TTA CAA GAA TTG AAA CTG AGT GGT GTG GTT CTC AAT GAA CAA  720
110  Ser Val Leu Gln Glu Leu Lys Leu Ser Gly Val Val Leu Asn Glu Gln  125

721  CCT GAG TAC AGT GCA GTA ATG AAG CAA ATA TTA GAA GAA TTC AAA AAT  768
126  Pro Glu Tyr Ser Ala Val Met Lys Gln Ile Leu Glu Glu Phe Lys Asn  141

769  AGT AAG GGT TCC TAT ACT GCA AAA ATT TTT AAA CTT ACT ACC ACT TTG  816
142  Ser Lys Gly Ser Tyr Thr Ala Lys Ile Phe Lys Leu Thr Thr Thr Leu  157

817  ACT ATT CCT TAC TTT GGA CCA ACA GGA CCG AGT TGG CGG CTA ATT TGT  864
158  Thr Ile Pro Tyr Phe Gly Pro Thr Gly Pro Ser Trp Arg Leu Ile Cys  173

865  CTT CCA GAA GAG CAC ACA GAA AAG TGG AGA AAA TTT ATC TTT GTA TCT  912
174  Leu Pro Glu Glu His Thr Glu Lys Trp Arg Lys Phe Ile Phe Val Ser  189

913  AAT CAT TGC ATG TCT GAT GGT CGG TCT TCG ATC CAC TTT TTT CAT GAT  960
190  Asn His Cys Met Ser Asp Gly Arg Ser Ser Ile His Phe Phe His Asp  205

961  TTA AGA GAC GAA TTA AAT AAT ATT AAA ACT CCA CCA AAA AAA TTA GAT  1008
206  Leu Arg Asp Glu Leu Asn Asn Ile Lys Thr Pro Pro Lys Lys Leu Asp  221
```

FIG. 2(d)

```
1009  TAC ATT TTC AAG TAC GAG GAT TAC CAA TTA TTG AGG AAA CTT CCA  1056
 222  Tyr Ile Phe Lys Tyr Glu Asp Tyr Gln Leu Leu Arg Lys Leu Pro   237

1057  GAA CCG ATC GAA AAG GTG ATA GAC TTT AGA CCA CCG TAC TTG TTT ATT  1104
 238  Glu Pro Ile Glu Lys Val Ile Asp Phe Arg Pro Pro Tyr Leu Phe Ile   253

1105  CCG AAG TCA CTT CTT TCG GGT TTC ATC TAC AAT CAT TTG AGA TTT TCT  1152
 254  Pro Lys Ser Leu Leu Ser Gly Phe Ile Tyr Asn His Leu Arg Phe Ser   269

1153  TCA AAA GGT GTC TGT ATG AGA ATG GAT GAT GTG GAA AAA ACC GAT GAT  1200
 270  Ser Lys Gly Val Cys Met Arg Met Asp Asp Val Glu Lys Thr Asp Asp   285

1201  GTT GTC ACC GAG ATC ATC AAT ATT TCA CCA ACA GAA TTT CAA GCG ATT  1248
 286  Val Val Thr Glu Ile Ile Asn Ile Ser Pro Thr Glu Phe Gln Ala Ile   301

1249  AAA GCA AAT ATT AAA TCA AAT ATC CAA GGT AAG TGT ACT ATC ACT CCG  1296
 302  Lys Ala Asn Ile Lys Ser Asn Ile Gln Gly Lys Cys Thr Ile Thr Pro   317

1297  TTT TTA CAT GTT TGT TGG TTT GTA TCT CTT CAT AAA TGG GGT AAA TTT  1344
 318  Phe Leu His Val Cys Trp Phe Val Ser Leu His Lys Trp Gly Lys Phe   333
```

FIG. 2(e)

```
1345  TTC AAA CCA TTG AAC TTC GAA TGG CTT ACG GAT ATT TTT ATC CCC GCA  1392
334   Phe Lys Pro Leu Asn Phe Glu Trp Leu Thr Asp Ile Phe Ile Pro Ala  349

1393  GAT TGC CGC TCA CAA CTA CCA GAT GAT GAA ATG AGA CAG ATG TAC      1440
350   Asp Cys Arg Ser Gln Leu Pro Asp Asp Glu Met Arg Gln Met Tyr      365

1441  AGA TAT GGC GCT AAC GTT GGA TTT ATT GAC TTC ATA GAC TTC ATA AGC  1488
366   Arg Tyr Gly Ala Asn Val Gly Phe Ile Asp Phe Ile Ser              381

1489  GAA TTT GAC ATG AAT GAT AAC AAA GAA AAT TTT TGG CCA CTT ATT GAG  1536
382   Glu Phe Asp Met Asn Asp Asn Lys Glu Asn Phe Trp Pro Leu Ile Glu  397

1537  CAC TAC CAT GAA GTA ATT TCG GAA GCT TTA AGA AAT AAA AAG CAT CTC  1584
398   His Tyr His Glu Val Ile Ser Glu Ala Leu Arg Asn Lys Lys His Leu  413

1585  CAT GGC TTA GGG TTC AAT ATA CAA GGC TTC GTT CAA AAA TAT GTG AAC  1632
414   His Gly Leu Gly Phe Asn Ile Gln Gly Phe Val Gln Lys Tyr Val Asn  429

1633  ATT GAC AAG GTA ATG TGC GAT CGT GCC ATC GGG AAA AGA CGC GGA GGT  1680
430   Ile Asp Lys Val Met Cys Asp Arg Ala Ile Gly Lys Arg Arg Gly Gly  445
```

FIG. 2(f)

```
1681  ACA TTG TTA AGC AAT GTA GGT CTG TTT AAT CAG TTA GAG GAG CCC GAT  1728
446   Thr Leu Leu Ser Asn Val Gly Leu Phe Asn Gln Leu Glu Glu Pro Asp  461

1729  GCC AAA TAT TCT ATA TGC GAT TTG GCA TTT GGC CAA TTT CAA GGA TCC  1776
462   Ala Lys Tyr Ser Ile Cys Asp Leu Ala Phe Gly Gln Phe Gln Gly Ser  477

1777  TGG CAC CAA GCA TTT TCC TTG GGT GTT TGT TCG ACT AAT GTA AAG GGG  1824
478   Trp His Gln Ala Phe Ser Leu Gly Val Cys Ser Thr Asn Val Lys Gly  493

B →
1825  ATG AAT ATT GTT GCT TCA ACA AAG AAT GTT GTT GGT AGT CAA GAA      1872
494   Met Asn Ile Val Ala Ser Thr Lys Asn Val Val Gly Ser Gln Glu      509

1873  TCT CTC GAA GAG CTT TGC TCC ATT TAC AAA GCT CTC CTT TTA GGC CCT  1920
510   Ser Leu Glu Glu Leu Cys Ser Ile Tyr Lys Ala Leu Leu Leu Gly Pro  525

1921  TAG ATC TCA CAT GAT GCT TGA CTG ATA TTA TTC GAC AAT ATG ATT ATG  1968
526   ***

1969  TCG TGT
```

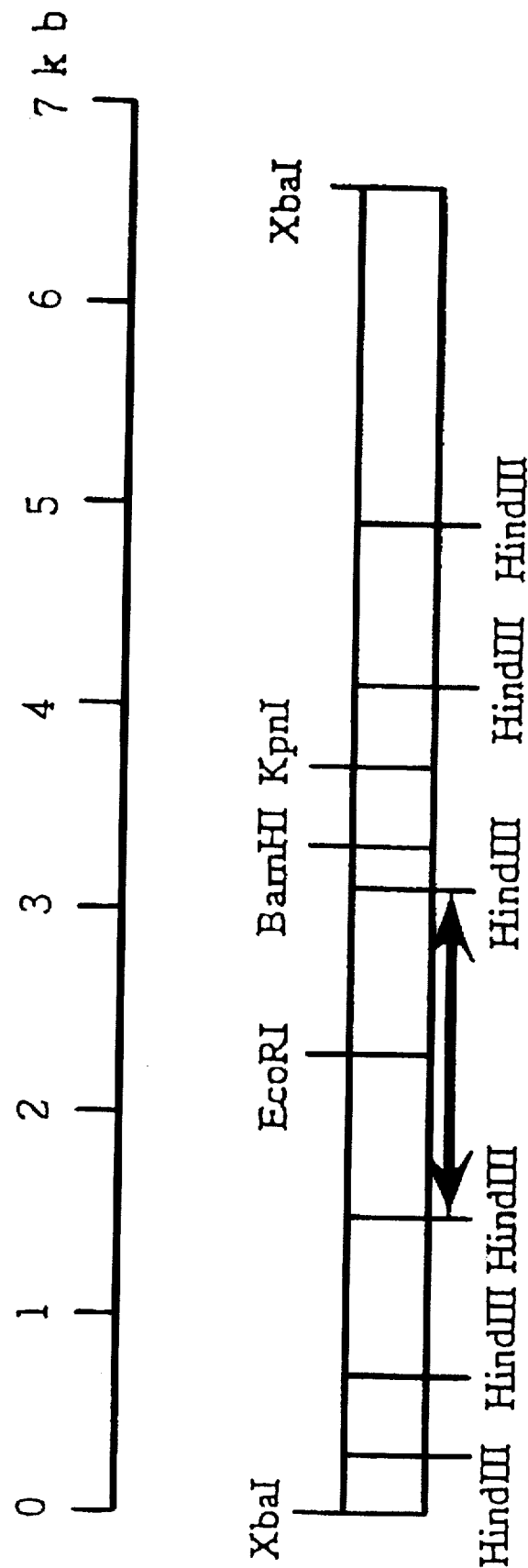
F I G. 3

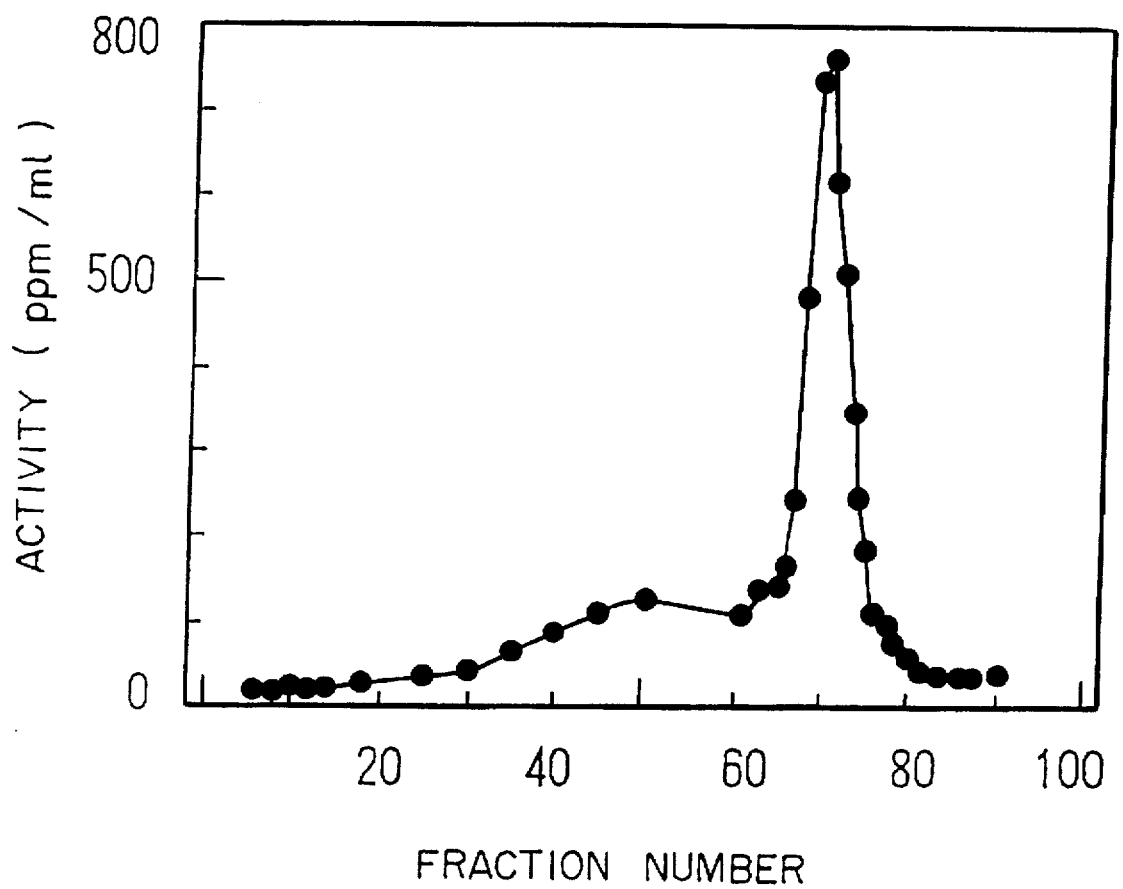
F I G. 7

FIG. 17(a)

```
          10         20         30         40         50         60
CTTGAACATTGATCAATGTGAAATACTGATTGATGTTCAATATATTGCTGATCTTAG 70         80         90        100        110        120
GGTGATTGGTAACCAAAATGCCGTCGGGCATTGTTCTAAAGGCTTGTGATTTGTAAGT 130        140        150        160        170        180
TTTTTGATCGCCTATTGTTTTTGGGCTGGCATCAGCATCGCGTGGAGCGAAGTCCAAATA 190        200        210        220        230        240
TGTTTTCTATTGTTTTTCATGGCTCTCTTCGAGAAGCGTCTTTTTAAAGCCAACCCAACAA 250        260        270        280        290        300
AACTTGAGACATGGAAACAGAGAAAGCCCAATTTAGCAGTATAACAAAAATCATCAATCC
                          A
                          ↓
         310        320        330        340        350        360
AAAAACTCTAATGAATACCTACAGTGAAAAAACGTCTCTTGTTCAAGATGAATGTCTTGT
             MetAsnThrTyrSerGluLysThrLeuValGlnAspGluCysLeuVal
  B
  ↓
         370        380        390        400        410        420
CAAGATGATACAGAATGGGCATTCCCGGCTATGGGATCTGTGGAAGATTTGTACGCTGC
LysMetIleGlnAsnGlyHisSerArgArgMetGlySerValGluAspLeuTyrAlaAla
```

FIG. 17(b)

```
         430       440       450       460       470       480
ACTCAACAGACAGAAATTGTATCGGAATTTTCGACATATTCAGAGCTGAATGATTACTG
LeuAsnArgGlnLysLeuTyrArgAsnPheSerThrTyrSerGluLeuAsnAspTyrCys 490       500       510       520       530       540
TACCAAAGATCAGCTCGCATTAGCTCTAAGAAATATATGTTTGAAAATCCGACTCTCCT
ThrLysAspGlnLeuAlaLeuAlaLeuArgAsnIleCysLeuLysAsnProThrLeuLeu 550       560       570       580       590       600
ACATATTGTATTACCGGCAAGATGGCCAGATCATGAAAAGTATTACCTTAGCTCAGAATA
HisIleValLeuProAlaArgTrpProAspHisGluLysTyrTyrLeuSerSerGluTyr 610       620       630       640       650       660
TTATTCACAGCCCCGTCCAAAACATGATTATATTTCGGTTTTGCCTGAGTTGAAATTAGA
TyrSerGlnProArgProLysHisAspTyrIleSerValLeuProGluLeuLysLeuAsp 670       680       690       700       710       720
TGGTGTGATTCTCAACGAGCAACCTGAGCACAATGCCCTAATGAAGCAAATACTAGAAGA
GlyValIleLeuAsnGluGlnProGluHisAsnAlaLeuMetLysGlnIleLeuGluGlu
```

FIG. 17(c)

```
        730        740        750        760        770        780
ATTGCGAATAGCAATGGATCTTATACTGCAAAATCTTTAAATTGACCACCGCTTTGAC
 PheAlaAsnSerAsnGlySerTyrThrAlaLysIlePheLysLeuThrThrAlaLeuThr 790        800        810        820        830        840
TATACCTTACACTGGGCCAACAAGTCCAACTTGGCGGTTGATTGTCTCCCAGAAGAAGA
 IleProTyrThrGlyProThrSerProThrTrpArgLeuIleCysLeuProCysLeuGluAsp 850        860        870        880        890        900
TGACACGAATAAGTGGAAGAAATTTATATTTGTATCCAATCACTGCATGTGCGATGGTAG
 AspThrAsnLysTrpLysLysPheIlePheValSerAsnHisCysMetCysAspGlyArg 910        920        930        940        950        960
ATCCTCAATTCACTTTTTCAGGATCTAAGAGATGAATTAAACAACATAAAACTCTGCC
 SerSerIleHisPhePheGlnAspLeuArgAspLeuAsnAsnIleLysThrLeuPro 970        980        990       1000       1010       1020
AAAGAAATTGGACTACATTTTCGAGTACGAAAAGGATTACCAACTTTGAGAAAGCTCCC
 LysLysLeuAspTyrIlePheGluTyrGluLysAspTyrGlnLeuLeuArgLysLeuPro 1030       1040       1050       1060       1070       1080
AGAACCCATTGAAAATATGATAGATTTCAGGCCGCCATATTGTTATTCCGAAGTCTCT
 GluProIleGluAsnMetIleAspPheArgProProTyrLeuPheIleProLysSerLeu
```

FIG. 17(d)

```
            1090      1100      1110      1120      1130      1140
        TCTTCTGGTTTATTTACAGTCATTGAGGTTTCTTCAAAGGGTGTTGCACGAGAAT
         LeuSerGlyPheIleTyrSerHisLeuArgPheSerSerLysGlyValCysThrArgMet 1150      1160      1170      1180      1190      1200
        GGATGAGATAGAAAAAGTGATGAGATTGTTACAGAAATTATCAATATTCCTCCATCAGA
         AspGluIleGluLysSerAspGluIleValThrGluIleIleAsnIleSerProSerGlu 1210      1220      1230      1240      1250      1260
        GTTTCAAAAAATTAGAACGAAAATTAAATTAAACATTCCCGGTAAGTGCACCACCACTCC
         PheGlnLysIleArgThrLysIleLeuAsnIleProGlyLysCysThrIleThrPro 1270      1280      1290      1300      1310      1320
        GTTCTTAGAAGTTGTTGGTTTGGTTGTTACTCTCCATAAATGGGGCAAGTTTTCAAACCACT
         PheLeuGluValCysTrpPheValThrLeuHisLysTrpGlyLysPheLysProLeu 1330      1340      1350      1360      1370      1380
        GAAGTTCGAGTGGCTCACTGATGTTTTATACCTGCAGATTGCCGCTCATTGCTGCCTGA
         LysPheGluTrpLeuThrAspValPheIleProAlaAspCysArgSerLeuLeuProGlu
```

FIG. 17(e)

```
      1390      1400      1410      1420      1430      1440
AGATGAAGAAGTGAGAGCTATGTACAGGTACGGCGCTAACGTTGGGTTTGTTGACTTCAC
AspGluValArgAlaMetTyrArgTyrGlyAlaAsnValGlyPheValAspPheThr 1450      1460      1470      1480      1490      1500
TCCATGGATAAGCAAATTCAACATGAACGACAGCAAAGAAAATTTCTGGCCACTTATTGC
ProTrpIleSerLysPheAsnMetAsnAspSerLysGluAsnPheTrpProLeuIleAla 1510      1520      1530      1540      1550      1560
ACATTATCATGAAGTAATTTCCGGGGCGATAAAGACAAGAAGCATCTCAATGGTTTGGG
HisTyrHisGluValIleSerGlyAlaIleLysAspLysLysHisLeuAsnGlyLeuGly 1570      1580      1590      1600      1610      1620
GTTCAACATACAAAGCTTGGTCCAAAGTATGTCAACATTGATAAAGTAATGCCTGATCG
PheAsnIleGlnSerLeuValGlnLysTyrValAsnIleAspLysValMetArgAspArg 1630      1640      1650      1660      1670      1680
TGCTCTTGGTAAATCACGTGGGGGCACTTTGTTGAGCAACGTAGGTATGTTCCACCAATC
AlaLeuGlyLysSerArgGlyGlyThrLeuLeuSerAsnValGlyMetPheHisGlnSer 1690      1700      1710      1720      1730      1740
GGAGGAGACCGAACACAAGTATCGTATAAGAGATTTGGCCTTTGGTCAATTTCAAGGGTC
GluGluThrGluHisLysTyrArgIleArgAspLeuAlaPheGlyGlnPheGlnGlySer
```

FIG. 17(f)

```
              1750      1760      1770      1780      1790      1800
ATGGCATCAAGCTTTTCATTGGGTGTGTTTCTTCGACTAATGTGAAGGGAATGAACATTTT
TrpHisGlnAlaPheSerLeuGlyValSerSerThrAsnValLysGlyMetAsnIleLeu 1810      1820      1830      1840      1850      1860
GATTTCTTCAACGAAAAATGTCGTGGGTAGTCAAGAATTGTTGGAGGAACTTTGTGCTAT
IleSerSerThrLysAsnValValGlySerGlnGluLeuLeuGluLeuCysAlaMet 1870      1880     ↓1890      1900      1910      1920
GTACAAGGCTCTGCTTTTAAATCCCTGATTCTTCTAAGACAATATGATGGTGGATACCTT
TyrLysAlaLeuLeuLeuAsnPro 1930      1940      1950      1960      1970      1980
TAAAAATTATAGTTATATTGTAGGGCTATCCCTGTTTTGATATTATAATGTTTTTTAGCT 1990      2000      2010      2020      2030      2040
TGTAGAGAGAAATGGTATCAGTTTTCTTTTACTAAGATTCGAACTAATCAATATCTCAAAG 2050      2060      2070      2080
TGATTAAACGACGTGTGTAAGGTAAGTAAGTGTACAGAAA
```

5,686,284

SEQUENCE LISTING ( 1 ) GENERAL INFORMATION:

( i i i ) NUMBER OF SEQUENCES: 19

( 2 ) INFORMATION FOR SEQ ID NO:1:

( i ) SEQUENCE CHARACTERISTICS:
        ( A ) LENGTH: 6 amino acids
        ( B ) TYPE: amino acid
        ( D ) TOPOLOGY: linear ( x i ) SEQUENCE DESCRIPTION: SEQ ID NO:1:

```
Lys  Tyr  Val  Asn  Ile  Asp
1                   5
```

( 2 ) INFORMATION FOR SEQ ID NO:2:

( i ) SEQUENCE CHARACTERISTICS:
        ( A ) LENGTH: 11 amino acids
        ( B ) TYPE: amino acid
        ( D ) TOPOLOGY: linear ( x i ) SEQUENCE DESCRIPTION: SEQ ID NO:2:

```
Lys  Asn  Gln  Ala  Pro  Val  Gln  Gln  Glu  Cys  Leu
1                   5                        10
```

( 2 ) INFORMATION FOR SEQ ID NO:3:

( i ) SEQUENCE CHARACTERISTICS:
        ( A ) LENGTH: 9 amino acids
        ( B ) TYPE: amino acid
        ( D ) TOPOLOGY: linear ( x i ) SEQUENCE DESCRIPTION: SEQ ID NO:3:

```
Lys  Gly  Met  Asn  Ile  Val  Val  Ala  Ser
1                   5
```

( 2 ) INFORMATION FOR SEQ ID NO:4:

( i ) SEQUENCE CHARACTERISTICS:
        ( A ) LENGTH: 11 amino acids
        ( B ) TYPE: amino acid
        ( D ) TOPOLOGY: linear ( x i ) SEQUENCE DESCRIPTION: SEQ ID NO:4:

```
Lys  Tyr  Glu  Glu  Asp  Tyr  Gln  Leu  Leu  Arg  Lys
1                   5                        10
```

( 2 ) INFORMATION FOR SEQ ID NO:5:

( i ) SEQUENCE CHARACTERISTICS:
        ( A ) LENGTH: 8 amino acids
        ( B ) TYPE: amino acid
        ( D ) TOPOLOGY: linear ( x i ) SEQUENCE DESCRIPTION: SEQ ID NO:5:

```
Lys  Gln  Ile  Leu  Glu  Glu  Phe  Lys
1                   5
```

(2) INFORMATION FOR SEQ ID NO:6:

(i) SEQUENCE CHARACTERISTICS:
        (A) LENGTH: 7 amino acids
        (B) TYPE: amino acid
        (D) TOPOLOGY: linear (xi) SEQUENCE DESCRIPTION: SEQ ID NO:6:

```
Lys  Leu  Asp  Tyr  Ile  Phe  Lys
1                  5
```

(2) INFORMATION FOR SEQ ID NO:7:

(i) SEQUENCE CHARACTERISTICS:
        (A) LENGTH: 10 amino acids
        (B) TYPE: amino acid
        (D) TOPOLOGY: linear (xi) SEQUENCE DESCRIPTION: SEQ ID NO:7:

```
Lys  Val  Met  Cys  Asp  Arg  Ala  Ile  Gly  Lys
1                  5                        10
```

(2) INFORMATION FOR SEQ ID NO:8:

(i) SEQUENCE CHARACTERISTICS:
        (A) LENGTH: 13 amino acids
        (B) TYPE: amino acid
        (D) TOPOLOGY: linear (xi) SEQUENCE DESCRIPTION: SEQ ID NO:8:

```
Lys  Leu  Ser  Gly  Val  Val  Leu  Asn  Glu  Gln  Pro  Glu  Tyr
1                  5                        10
```

(2) INFORMATION FOR SEQ ID NO:9:

(i) SEQUENCE CHARACTERISTICS:
        (A) LENGTH: 18 amino acids
        (B) TYPE: amino acid
        (D) TOPOLOGY: linear (xi) SEQUENCE DESCRIPTION: SEQ ID NO:9:

```
Lys  Asn  Val  Val  Gly  Ser  Gln  Glu  Ser  Leu  Glu  Glu  Leu  Cys  Ser  Ile
1                  5                        10                       15

Tyr  Lys
```

(2) INFORMATION FOR SEQ ID NO:10:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:10:

AARTAYGARG ARGAYTAYCA     20

(2) INFORMATION FOR SEQ ID NO:11:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:11:

AARTAYGTNA AYATHGA     17

(2) INFORMATION FOR SEQ ID NO:12:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:12:

```
CTCAATGAAC AACCTGAG                                                  18
```

(2) INFORMATION FOR SEQ ID NO:13:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:13:

```
TCTTCGAGAG ATTCTTGG                                                  18
```

(2) INFORMATION FOR SEQ ID NO:14:

(i) SEQUENCE CHARACTERISTICS:
        (A) LENGTH: 1923 base pairs
        (B) TYPE: nucleic acid
        (C) STRANDEDNESS: double
        (D) TOPOLOGY: linear (ix) FEATURE:
        (A) NAME/KEY: CDS
        (B) LOCATION: 234..1811

(xi) SEQUENCE DESCRIPTION: SEQ ID NO:14:

```
AGCGTGTGAG GACTACTCAT TGGCTTGCGA TTTACGGTTT TTATATTTTT TGCCGCACAT    60

CATTTTTGG CCTGGTATTG TCATCGCGTT GAGCGGACTC TGAATATAAT CCTATTGTTT    120

TTTATGGATC TCTGGAAGCG TCTTTTTGAA GCCAACCCAA CAAAAATTCG AGACAAGAAA   180

ATAAAAAACG GCACTTCATC AGTATCACAA ATACCATCAA TTTATCAGCT CTC ATG     236
                                                          Met
                                                           1

AAT GAA ATC GAT GAG AAA AAT CAG GCC CCC GTG CAA CAA GAA TGC CTG    284
Asn Glu Ile Asp Glu Lys Asn Gln Ala Pro Val Gln Gln Glu Cys Leu
              5                  10                  15

AAA GAG ATG ATT CAG AAT GGG CAT GCT CGG CGT ATG GGA TCT GTT GAA    332
Lys Glu Met Ile Gln Asn Gly His Ala Arg Arg Met Gly Ser Val Glu
         20                  25                  30

GAT CTG TAT GTT GCT CTC AAC AGA CAA AAC TTA TAT CGG AAC TTC TGC    380
Asp Leu Tyr Val Ala Leu Asn Arg Gln Asn Leu Tyr Arg Asn Phe Cys
     35                  40                  45

ACA TAT GGA GAA TTG AGT GAT TAC TGT ACT AGG GAT CAG CTC ACA TTA    428
Thr Tyr Gly Glu Leu Ser Asp Tyr Cys Thr Arg Asp Gln Leu Thr Leu
 50                  55                  60                  65

GCT TTG AGG GAA ATC TGC CTG AAA AAT CCA ACT CTT TTA CAT ATT GTT    476
Ala Leu Arg Glu Ile Cys Leu Lys Asn Pro Thr Leu Leu His Ile Val
                 70                  75                  80

CTA CCA ATA AGA TGG CCA AAT CAT GAA AAT TAT TAT CGC AGT TCC GAA    524
Leu Pro Ile Arg Trp Pro Asn His Glu Asn Tyr Tyr Arg Ser Ser Glu
             85                  90                  95

TAC TAT TCA CGG CCA CAT CCA GTG CAT GAT TAT ATT TCA GTA TTA CAG    572
Tyr Tyr Ser Arg Pro His Pro Val His Asp Tyr Ile Ser Val Leu Gln
        100                 105                 110

GAA TTG AAA CTG AGT GGT GTG GTT CTC AAT GAA CAA CCT GAG TAC AGT    620
```

|  |  |  |  |  |  |  |  |  |  |  |  |  |  |  |  |
|---|---|---|---|---|---|---|---|---|---|---|---|---|---|---|---|
| Glu | Leu | Lys | Leu | Ser | Gly | Val | Val | Leu | Asn | Glu | Gln | Pro | Glu | Tyr | Ser |
| 115 |  |  |  |  | 120 |  |  |  |  | 125 |  |  |  |  |  |

| GCA | GTA | ATG | AAG | CAA | ATA | TTA | GAA | GAA | TTC | AAA | AAT | AGT | AAG | GGT | TCC | 668 |
|---|---|---|---|---|---|---|---|---|---|---|---|---|---|---|---|---|
| Ala | Val | Met | Lys | Gln | Ile | Leu | Glu | Glu | Phe | Lys | Asn | Ser | Lys | Gly | Ser |  |
| 130 |  |  |  |  | 135 |  |  |  |  | 140 |  |  |  |  | 145 |  |

| TAT | ACT | GCA | AAA | ATT | TTT | AAA | CTT | ACT | ACC | ACT | TTG | ACT | ATT | CCT | TAC | 716 |
|---|---|---|---|---|---|---|---|---|---|---|---|---|---|---|---|---|
| Tyr | Thr | Ala | Lys | Ile | Phe | Lys | Leu | Thr | Thr | Thr | Leu | Thr | Ile | Pro | Tyr |  |
|  |  |  |  | 150 |  |  |  |  | 155 |  |  |  |  | 160 |  |  |

| TTT | GGA | CCA | ACA | GGA | CCG | AGT | TGG | CGG | CTA | ATT | TGT | CTT | CCA | GAA | GAG | 764 |
|---|---|---|---|---|---|---|---|---|---|---|---|---|---|---|---|---|
| Phe | Gly | Pro | Thr | Gly | Pro | Ser | Trp | Arg | Leu | Ile | Cys | Leu | Pro | Glu | Glu |  |
|  |  |  | 165 |  |  |  |  | 170 |  |  |  |  | 175 |  |  |  |

| CAC | ACA | GAA | AAG | TGG | AAA | AAA | TTT | ATC | TTT | GTA | TCT | AAT | CAT | TGC | ATG | 812 |
|---|---|---|---|---|---|---|---|---|---|---|---|---|---|---|---|---|
| His | Thr | Glu | Lys | Trp | Lys | Lys | Phe | Ile | Phe | Val | Ser | Asn | His | Cys | Met |  |
|  |  | 180 |  |  |  |  | 185 |  |  |  |  | 190 |  |  |  |  |

| TCT | GAT | GGT | CGG | TCT | TCG | ATC | CAC | TTT | TTT | CAT | GAT | TTA | AGA | GAC | GAA | 860 |
|---|---|---|---|---|---|---|---|---|---|---|---|---|---|---|---|---|
| Ser | Asp | Gly | Arg | Ser | Ser | Ile | His | Phe | Phe | His | Asp | Leu | Arg | Asp | Glu |  |
|  | 195 |  |  |  |  | 200 |  |  |  |  | 205 |  |  |  |  |  |

| TTA | AAT | AAT | ATT | AAA | ACT | CCA | CCA | AAA | AAA | TTA | GAT | TAC | ATT | TTC | AAG | 908 |
|---|---|---|---|---|---|---|---|---|---|---|---|---|---|---|---|---|
| Leu | Asn | Asn | Ile | Lys | Thr | Pro | Pro | Lys | Lys | Leu | Asp | Tyr | Ile | Phe | Lys |  |
| 210 |  |  |  |  | 215 |  |  |  |  | 220 |  |  |  |  | 225 |  |

| TAC | GAG | GAG | GAT | TAC | CAA | TTG | TTG | AGG | AAA | CTT | CCA | GAA | CCG | ATC | GAA | 956 |
|---|---|---|---|---|---|---|---|---|---|---|---|---|---|---|---|---|
| Tyr | Glu | Glu | Asp | Tyr | Gln | Leu | Leu | Arg | Lys | Leu | Pro | Glu | Pro | Ile | Glu |  |
|  |  |  |  | 230 |  |  |  |  | 235 |  |  |  |  | 240 |  |  |

| AAG | GTG | ATA | GAC | TTT | AGA | CCA | CCG | TAC | TTG | TTT | ATT | CCG | AAG | TCA | CTT | 1004 |
|---|---|---|---|---|---|---|---|---|---|---|---|---|---|---|---|---|
| Lys | Val | Ile | Asp | Phe | Arg | Pro | Pro | Tyr | Leu | Phe | Ile | Pro | Lys | Ser | Leu |  |
|  |  |  | 245 |  |  |  |  | 250 |  |  |  |  | 255 |  |  |  |

| CTT | TCG | GGT | TTC | ATC | TAC | AAT | CAT | TTG | AGA | TTT | TCT | TCA | AAA | GGT | GTC | 1052 |
|---|---|---|---|---|---|---|---|---|---|---|---|---|---|---|---|---|
| Leu | Ser | Gly | Phe | Ile | Tyr | Asn | His | Leu | Arg | Phe | Ser | Ser | Lys | Gly | Val |  |
|  |  | 260 |  |  |  |  | 265 |  |  |  |  | 270 |  |  |  |  |

| TGT | ATG | AGA | ATG | GAT | GAT | GTG | GAA | AAA | ACC | GAT | GAT | GTT | GTC | ACC | GAG | 1100 |
|---|---|---|---|---|---|---|---|---|---|---|---|---|---|---|---|---|
| Cys | Met | Arg | Met | Asp | Asp | Val | Glu | Lys | Thr | Asp | Asp | Val | Val | Thr | Glu |  |
|  | 275 |  |  |  |  | 280 |  |  |  |  | 285 |  |  |  |  |  |

| ATC | ATC | AAT | ATT | TCA | CCA | ACA | GAA | TTT | CAA | GCG | ATT | AAA | GCA | AAT | ATT | 1148 |
|---|---|---|---|---|---|---|---|---|---|---|---|---|---|---|---|---|
| Ile | Ile | Asn | Ile | Ser | Pro | Thr | Glu | Phe | Gln | Ala | Ile | Lys | Ala | Asn | Ile |  |
| 290 |  |  |  |  | 295 |  |  |  |  | 300 |  |  |  |  | 305 |  |

| AAA | TCA | AAT | ATC | CAA | GGT | AAG | TGT | ACT | ATC | ACT | CCG | TTT | TTA | CAT | GTT | 1196 |
|---|---|---|---|---|---|---|---|---|---|---|---|---|---|---|---|---|
| Lys | Ser | Asn | Ile | Gln | Gly | Lys | Cys | Thr | Ile | Thr | Pro | Phe | Leu | His | Val |  |
|  |  |  |  | 310 |  |  |  |  | 315 |  |  |  |  | 320 |  |  |

| TGT | TGG | TTT | GTA | TCT | CTT | CAT | AAA | TGG | GGT | AAA | TTT | TTC | AAA | CCA | TTG | 1244 |
|---|---|---|---|---|---|---|---|---|---|---|---|---|---|---|---|---|
| Cys | Trp | Phe | Val | Ser | Leu | His | Lys | Trp | Gly | Lys | Phe | Phe | Lys | Pro | Leu |  |
|  |  |  | 325 |  |  |  |  | 330 |  |  |  |  | 335 |  |  |  |

| AAC | TTC | GAA | TGG | CTT | ACG | GAT | ATT | TTT | ATC | CCC | GCA | GAT | TGC | CGC | TCA | 1292 |
|---|---|---|---|---|---|---|---|---|---|---|---|---|---|---|---|---|
| Asn | Phe | Glu | Trp | Leu | Thr | Asp | Ile | Phe | Ile | Pro | Ala | Asp | Cys | Arg | Ser |  |
|  |  | 340 |  |  |  |  | 345 |  |  |  |  | 350 |  |  |  |  |

| CAA | CTA | CCA | GAT | GAT | GAT | GAA | ATG | AGA | CAG | ATG | TAC | AGA | TAT | GGC | GCT | 1340 |
|---|---|---|---|---|---|---|---|---|---|---|---|---|---|---|---|---|
| Gln | Leu | Pro | Asp | Asp | Asp | Glu | Met | Arg | Gln | Met | Tyr | Arg | Tyr | Gly | Ala |  |
|  | 355 |  |  |  |  | 360 |  |  |  |  | 365 |  |  |  |  |  |

| AAC | GTT | GGA | TTT | ATT | GAC | TTC | ACC | CCA | TGG | ATA | AGC | GAA | TTT | GAC | ATG | 1388 |
|---|---|---|---|---|---|---|---|---|---|---|---|---|---|---|---|---|
| Asn | Val | Gly | Phe | Ile | Asp | Phe | Thr | Pro | Trp | Ile | Ser | Glu | Phe | Asp | Met |  |
| 370 |  |  |  |  | 375 |  |  |  |  | 380 |  |  |  |  | 385 |  |

| AAT | GAT | AAC | AAA | GAA | AAA | TTT | TGG | CCA | CTT | ATT | GAG | CAC | TAC | CAT | GAA | 1436 |
|---|---|---|---|---|---|---|---|---|---|---|---|---|---|---|---|---|
| Asn | Asp | Asn | Lys | Glu | Lys | Phe | Trp | Pro | Leu | Ile | Glu | His | Tyr | His | Glu |  |
|  |  |  | 390 |  |  |  |  | 395 |  |  |  |  | 400 |  |  |  |

| GTA | ATT | TCG | GAA | GCT | TTA | AGA | AAT | AAA | AAG | CAC | CTC | CAT | GGC | TTA | GGG | 1484 |
|---|---|---|---|---|---|---|---|---|---|---|---|---|---|---|---|---|
| Val | Ile | Ser | Glu | Ala | Leu | Arg | Asn | Lys | Lys | His | Leu | His | Gly | Leu | Gly |  |
|  |  |  | 405 |  |  |  |  | 410 |  |  |  |  | 415 |  |  |  |

| TTC | AAT | ATA | CAA | GGC | TTC | GTT | CAA | AAA | TAT | GTG | AAT | ATT | GAC | AAG | GTA | 1532 |
|---|---|---|---|---|---|---|---|---|---|---|---|---|---|---|---|---|
| Phe | Asn | Ile | Gln | Gly | Phe | Val | Gln | Lys | Tyr | Val | Asn | Ile | Asp | Lys | Val |  |
|  |  |  | 420 |  |  |  |  | 425 |  |  |  |  | 430 |  |  |  |

| ATG | TGC | GAT | CGT | GCC | ATC | GGG | AAA | AGA | CGC | GGA | GGT | ACA | TTG | TTA | AGC | 1580 |

```
Met  Cys  Asp  Arg  Ala  Ile  Gly  Lys  Arg  Arg  Gly  Gly  Thr  Leu  Leu  Ser
     435                 440                 445

AAT  GTA  GGT  CTG  TTT  AAT  CAG  TTA  GAG  GAG  CCC  GAT  GCC  AAA  TAT  TCT      1628
Asn  Val  Gly  Leu  Phe  Asn  Gln  Leu  Glu  Glu  Pro  Asp  Ala  Lys  Tyr  Ser
450                      455                 460                      465

ATA  TGC  GAT  TTG  GCA  TTT  GGC  CAA  TTT  CAA  GGA  TCC  TGG  CAC  CAA  GCA      1676
Ile  Cys  Asp  Leu  Ala  Phe  Gly  Gln  Phe  Gln  Gly  Ser  Trp  His  Gln  Ala
                    470                 475                      480

TTT  TCC  TTG  GGT  GTT  TGT  TCG  ACT  AAT  GTA  AAG  GGG  ATG  AAT  ATT  GTT      1724
Phe  Ser  Leu  Gly  Val  Cys  Ser  Thr  Asn  Val  Lys  Gly  Met  Asn  Ile  Val
               485                 490                      495

GTT  GCT  TCA  ACA  AAA  AAT  GTT  GTT  GGT  AGC  CAA  GAA  TCT  CTC  GAA  GAG      1772
Val  Ala  Ser  Thr  Lys  Asn  Val  Val  Gly  Ser  Gln  Glu  Ser  Leu  Glu  Glu
          500                      505                      510

CTT  TGC  TCC  ATT  TAT  AAA  GCT  CTC  CTT  TTA  GGC  CCT  TAGATCTCAC              1818
Leu  Cys  Ser  Ile  Tyr  Lys  Ala  Leu  Leu  Leu  Gly  Pro
     515                 520                      525

ATGATGCTTG ACTGATATTA TTCGACAATA TGATTATGTC GTGTAAATAA CCCACTTTCA                    1878

TGTTGTCACT CCCTCGGCTT TGGTTGGTTA AAGGGACTTA TTGGT                                    1923
```

( 2 ) INFORMATION FOR SEQ ID NO:15:

( i ) SEQUENCE CHARACTERISTICS:
        ( A ) LENGTH: 525 amino acids
        ( B ) TYPE: amino acid
        ( D ) TOPOLOGY: linear ( i i ) MOLECULE TYPE: protein ( x i ) SEQUENCE DESCRIPTION: SEQ ID NO:15:

```
Met  Asn  Glu  Ile  Asp  Glu  Lys  Asn  Gln  Ala  Pro  Val  Gln  Gln  Glu  Cys
 1                  5                   10                       15

Leu  Lys  Glu  Met  Ile  Gln  Asn  Gly  His  Ala  Arg  Arg  Met  Gly  Ser  Val
               20                  25                       30

Glu  Asp  Leu  Tyr  Val  Ala  Leu  Asn  Arg  Gln  Asn  Leu  Tyr  Arg  Asn  Phe
          35                      40                  45

Cys  Thr  Tyr  Gly  Glu  Leu  Ser  Asp  Tyr  Cys  Thr  Arg  Asp  Gln  Leu  Thr
     50                      55                      60

Leu  Ala  Leu  Arg  Glu  Ile  Cys  Leu  Lys  Asn  Pro  Thr  Leu  Leu  His  Ile
 65                      70                  75                            80

Val  Leu  Pro  Ile  Arg  Trp  Pro  Asn  His  Glu  Asn  Tyr  Tyr  Arg  Ser  Ser
               85                  90                            95

Glu  Tyr  Tyr  Ser  Arg  Pro  His  Pro  Val  His  Asp  Tyr  Ile  Ser  Val  Leu
               100                 105                 110

Gln  Glu  Leu  Lys  Leu  Ser  Gly  Val  Val  Leu  Asn  Glu  Gln  Pro  Glu  Tyr
               115                 120                 125

Ser  Ala  Val  Met  Lys  Gln  Ile  Leu  Glu  Glu  Phe  Lys  Asn  Ser  Lys  Gly
     130                 135                 140

Ser  Tyr  Thr  Ala  Lys  Ile  Phe  Lys  Leu  Thr  Thr  Leu  Thr  Ile  Pro
145                      150                 155                      160

Tyr  Phe  Gly  Pro  Thr  Gly  Pro  Ser  Trp  Arg  Leu  Ile  Cys  Leu  Pro  Glu
                    165                 170                 175

Glu  His  Thr  Glu  Lys  Trp  Lys  Lys  Phe  Ile  Phe  Val  Ser  Asn  His  Cys
               180                 185                 190

Met  Ser  Asp  Gly  Arg  Ser  Ser  Ile  His  Phe  Phe  His  Asp  Leu  Arg  Asp
          195                 200                 205

Glu  Leu  Asn  Asn  Ile  Lys  Thr  Pro  Pro  Lys  Lys  Leu  Asp  Tyr  Ile  Phe
210                      215                 220
```

| Lys<br>225 | Tyr | Glu | Glu | Asp<br>230 | Tyr | Gln | Leu | Leu | Arg<br>235 | Lys | Leu | Pro | Glu | Pro<br>240 | Ile |
| --- | --- | --- | --- | --- | --- | --- | --- | --- | --- | --- | --- | --- | --- | --- | --- |
| Glu | Lys | Val | Ile | Asp<br>245 | Phe | Arg | Pro | Pro | Tyr<br>250 | Leu | Phe | Ile | Pro | Lys<br>255 | Ser |
| Leu | Leu | Ser | Gly<br>260 | Phe | Ile | Tyr | Asn | His<br>265 | Leu | Arg | Phe | Ser | Ser<br>270 | Lys | Gly |
| Val | Cys | Met<br>275 | Arg | Met | Asp | Asp | Val<br>280 | Glu | Lys | Thr | Asp | Asp<br>285 | Val | Val | Thr |
| Glu | Ile<br>290 | Ile | Asn | Ile | Ser | Pro<br>295 | Thr | Glu | Phe | Gln | Ala<br>300 | Ile | Lys | Ala | Asn |
| Ile<br>305 | Lys | Ser | Asn | Ile | Gln<br>310 | Gly | Lys | Cys | Thr | Ile<br>315 | Thr | Pro | Phe | Leu | His<br>320 |
| Val | Cys | Trp | Phe | Val<br>325 | Ser | Leu | His | Lys | Trp<br>330 | Gly | Lys | Phe | Phe | Lys<br>335 | Pro |
| Leu | Asn | Phe | Glu<br>340 | Trp | Leu | Thr | Asp | Ile<br>345 | Phe | Ile | Pro | Ala | Asp<br>350 | Cys | Arg |
| Ser | Gln | Leu<br>355 | Pro | Asp | Asp | Asp | Glu<br>360 | Met | Arg | Gln | Met | Tyr<br>365 | Arg | Tyr | Gly |
| Ala | Asn<br>370 | Val | Gly | Phe | Ile | Asp<br>375 | Phe | Thr | Pro | Trp | Ile<br>380 | Ser | Glu | Phe | Asp |
| Met<br>385 | Asn | Asp | Asn | Lys | Glu<br>390 | Lys | Phe | Trp | Pro | Leu<br>395 | Ile | Glu | His | Tyr | His<br>400 |
| Glu | Val | Ile | Ser | Glu<br>405 | Ala | Leu | Arg | Asn | Lys<br>410 | Lys | His | Leu | His | Gly<br>415 | Leu |
| Gly | Phe | Asn | Ile<br>420 | Gln | Gly | Phe | Val | Gln<br>425 | Lys | Tyr | Val | Asn | Ile<br>430 | Asp | Lys |
| Val | Met | Cys<br>435 | Asp | Arg | Ala | Ile | Gly<br>440 | Lys | Arg | Arg | Gly | Gly<br>445 | Thr | Leu | Leu |
| Ser | Asn<br>450 | Val | Gly | Leu | Phe | Asn<br>455 | Gln | Leu | Glu | Glu | Pro<br>460 | Asp | Ala | Lys | Tyr |
| Ser | Ile | Cys<br>465 | Asp | Leu | Ala | Phe<br>470 | Gly | Gln | Phe | Gln | Gly<br>475 | Ser | Trp | His | Gln<br>480 |
| Ala | Phe | Ser | Leu | Gly<br>485 | Val | Cys | Ser | Thr | Asn<br>490 | Val | Lys | Gly | Met | Asn<br>495 | Ile |
| Val | Val | Ala | Ser<br>500 | Thr | Lys | Asn | Val | Val<br>505 | Gly | Ser | Gln | Glu | Ser<br>510 | Leu | Glu |
| Glu | Leu | Cys<br>515 | Ser | Ile | Tyr | Lys | Ala<br>520 | Leu | Leu | Leu | Gly | Pro<br>525 | | | |

( 2 ) INFORMATION FOR SEQ ID NO:16:

( i ) SEQUENCE CHARACTERISTICS:
      ( A ) LENGTH: 1974 base pairs
      ( B ) TYPE: nucleic acid
      ( C ) STRANDEDNESS: double
      ( D ) TOPOLOGY: linear ( i x ) FEATURE:
      ( A ) NAME/KEY: CDS
      ( B ) LOCATION: 346..1923

( x i ) SEQUENCE DESCRIPTION: SEQ ID NO:16:

| | | | | | |
| --- | --- | --- | --- | --- | --- |
| GTAGCTTCAT | TTGTTGGCAC | AGGACTATTC | CACCCTTAGA | ATTGACTTTT | TGGACATTGA | 60 |
| GCTAAGGTTC | AATGCACTCG | ATGGTCTTCT | CACTTCCGAA | TATATAGATC | TAGCGTGTGA | 120 |
| GGACTACTCA | TTGGCTTGCG | ATTTACGGTT | TTTATATTTT | TTGCCGCACA | TCATTTTTTG | 180 |
| GCCTGGTATT | GTCATCGCGG | TTGAGCGGAC | TCTGAATATA | ATCCTATTGT | TTTTTATGGA | 240 |

| | |
|---|---|
| TCTCTGGAAG CGTCTTTTTG AAGCCAACCC AACAAAAATT CGAGACAAGA AAATAAAAAA | 300 |
| CGGCACTTCA TCAGTATCAC AAATACCATC AATTTATCAG CTCTC ATG AAT GAA<br>                                                                                                                                                                                                                      Met Asn Glu<br>                                                                                                                                                                                                                       1 | 354 |

```
ATC GAT GAG AAA AAT CAG GCC CCC GTG CAA CAA GAA TGC CTG AAA GAG            402
Ile Asp Glu Lys Asn Gln Ala Pro Val Gln Gln Glu Cys Leu Lys Glu
         5              10               15

ATG ATT CAG AAT GGG CAT GCT CGG CGT ATG GGA TCT GTT GAA GAT CTG            450
Met Ile Gln Asn Gly His Ala Arg Arg Met Gly Ser Val Glu Asp Leu
 20              25              30                      35

TAT GTT GCT CTC AAC AGA CAA AAC TTA TAT CGA AAC TTC TGC ACA TAT            498
Tyr Val Ala Leu Asn Arg Gln Asn Leu Tyr Arg Asn Phe Cys Thr Tyr
             40              45                      50

GGA GAA TTG AGT GAT TAC TGT ACT AGG GAT CAG CTC ACA TTA GCT TTG            546
Gly Glu Leu Ser Asp Tyr Cys Thr Arg Asp Gln Leu Thr Leu Ala Leu
             55              60                      65

AGG GAA ATC TGC CTG AAA AAT CCA ACT CTT TTA CAT ATT GTT CTA CCA            594
Arg Glu Ile Cys Leu Lys Asn Pro Thr Leu Leu His Ile Val Leu Pro
         70              75                      80

ACA AGA TGG CCA AAT CAT GAA AAT TAT TAT CGC AGT TCC GAA TAC TAT            642
Thr Arg Trp Pro Asn His Glu Asn Tyr Tyr Arg Ser Ser Glu Tyr Tyr
 85              90                      95

TCA CGG CCA CAT CCA GTG CAT GAT TAT ATC TCA GTA TTA CAA GAA TTG            690
Ser Arg Pro His Pro Val His Asp Tyr Ile Ser Val Leu Gln Glu Leu
100             105             110                    115

AAA CTG AGT GGT GTG GTT CTC AAT GAA CAA CCT GAG TAC AGT GCA GTA            738
Lys Leu Ser Gly Val Val Leu Asn Glu Gln Pro Glu Tyr Ser Ala Val
             120             125                    130

ATG AAG CAA ATA TTA GAA GAA TTC AAA AAT AGT AAG GGT TCC TAT ACT            786
Met Lys Gln Ile Leu Glu Glu Phe Lys Asn Ser Lys Gly Ser Tyr Thr
             135             140                    145

GCA AAA ATT TTT AAA CTT ACT ACC ACT TTG ACT ATT CCT TAC TTT GGA            834
Ala Lys Ile Phe Lys Leu Thr Thr Thr Leu Thr Ile Pro Tyr Phe Gly
        150              155                    160

CCA ACA GGA CCG AGT TGG CGG CTA ATT TGT CTT CCA GAA GAG CAC ACA            882
Pro Thr Gly Pro Ser Trp Arg Leu Ile Cys Leu Pro Glu Glu His Thr
        165              170                    175

GAA AAG TGG AGA AAA TTT ATC TTT GTA TCT AAT CAT TGC ATG TCT GAT            930
Glu Lys Trp Arg Lys Phe Ile Phe Val Ser Asn His Cys Met Ser Asp
180             185             190                    195

GGT CGG TCT TCG ATC CAC TTT TTT CAT GAT TTA AGA GAC GAA TTA AAT            978
Gly Arg Ser Ser Ile His Phe Phe His Asp Leu Arg Asp Glu Leu Asn
            200             205                    210

AAT ATT AAA ACT CCA CCA AAA AAA TTA GAT TAC ATT TTC AAG TAC GAG            1026
Asn Ile Lys Thr Pro Pro Lys Lys Leu Asp Tyr Ile Phe Lys Tyr Glu
            215             220                    225

GAG GAT TAC CAA TTA TTG AGG AAA CTT CCA GAA CCG ATC GAA AAG GTG            1074
Glu Asp Tyr Gln Leu Leu Arg Lys Leu Pro Glu Pro Ile Glu Lys Val
        230             235                    240

ATA GAC TTT AGA CCA CCG TAC TTG TTT ATT CCG AAG TCA CTT CTT TCG            1122
Ile Asp Phe Arg Pro Pro Tyr Leu Phe Ile Pro Lys Ser Leu Leu Ser
        245             250                    255

GGT TTC ATC TAC AAT CAT TTG AGA TTT TCT TCA AAA GGT GTC TGT ATG            1170
Gly Phe Ile Tyr Asn His Leu Arg Phe Ser Ser Lys Gly Val Cys Met
260             265             270                    275

AGA ATG GAT GAT GTG GAA AAA ACC GAT GAT GTT GTC ACC GAG ATC ATC            1218
Arg Met Asp Asp Val Glu Lys Thr Asp Asp Val Val Thr Glu Ile Ile
            280             285                    290

AAT ATT TCA CCA ACA GAA TTT CAA GCG ATT AAA GCA AAT ATT AAA TCA            1266
```

```
Asn  Ile  Ser  Pro  Thr  Glu  Phe  Gln  Ala  Ile  Lys  Ala  Asn  Ile  Lys  Ser
               295                      300                      305

AAT  ATC  CAA  GGT  AAG  TGT  ACT  ATC  ACT  CCG  TTT  TTA  CAT  GTT  TGT  TGG     1314
Asn  Ile  Gln  Gly  Lys  Cys  Thr  Ile  Thr  Pro  Phe  Leu  His  Val  Cys  Trp
               310                      315                      320

TTT  GTA  TCT  CTT  CAT  AAA  TGG  GGT  AAA  TTT  TTC  AAA  CCA  TTG  AAC  TTC     1362
Phe  Val  Ser  Leu  His  Lys  Trp  Gly  Lys  Phe  Phe  Lys  Pro  Leu  Asn  Phe
     325                      330                      335

GAA  TGG  CTT  ACG  GAT  ATT  TTT  ATC  CCC  GCA  GAT  TGC  CGC  TCA  CAA  CTA     1410
Glu  Trp  Leu  Thr  Asp  Ile  Phe  Ile  Pro  Ala  Asp  Cys  Arg  Ser  Gln  Leu
340                      345                      350                      355

CCA  GAT  GAT  GAT  GAA  ATG  AGA  CAG  ATG  TAC  AGA  TAT  GGC  GCT  AAC  GTT     1458
Pro  Asp  Asp  Asp  Glu  Met  Arg  Gln  Met  Tyr  Arg  Tyr  Gly  Ala  Asn  Val
                    360                      365                      370

GGA  TTT  ATT  GAC  TTC  ACC  CCC  TGG  ATA  AGC  GAA  TTT  GAC  ATG  AAT  GAT     1506
Gly  Phe  Ile  Asp  Phe  Thr  Pro  Trp  Ile  Ser  Glu  Phe  Asp  Met  Asn  Asp
               375                      380                      385

AAC  AAA  GAA  AAT  TTT  TGG  CCA  CTT  ATT  GAG  CAC  TAC  CAT  GAA  GTA  ATT     1554
Asn  Lys  Glu  Asn  Phe  Trp  Pro  Leu  Ile  Glu  His  Tyr  His  Glu  Val  Ile
          390                      395                      400

TCG  GAA  GCT  TTA  AGA  AAT  AAA  AAG  CAT  CTC  CAT  GGC  TTA  GGG  TTC  AAT     1602
Ser  Glu  Ala  Leu  Arg  Asn  Lys  Lys  His  Leu  His  Gly  Leu  Gly  Phe  Asn
     405                      410                      415

ATA  CAA  GGC  TTC  GTT  CAA  AAA  TAT  GTG  AAC  ATT  GAC  AAG  GTA  ATG  TGC     1650
Ile  Gln  Gly  Phe  Val  Gln  Lys  Tyr  Val  Asn  Ile  Asp  Lys  Val  Met  Cys
420                      425                      430                      435

GAT  CGT  GCC  ATC  GGG  AAA  AGA  CGC  GGA  GGT  ACA  TTG  TTA  AGC  AAT  GTA     1698
Asp  Arg  Ala  Ile  Gly  Lys  Arg  Arg  Gly  Gly  Thr  Leu  Leu  Ser  Asn  Val
               440                      445                      450

GGT  CTG  TTT  AAT  CAG  TTA  GAG  GAG  CCC  GAT  GCC  AAA  TAT  TCT  ATA  TGC     1746
Gly  Leu  Phe  Asn  Gln  Leu  Glu  Glu  Pro  Asp  Ala  Lys  Tyr  Ser  Ile  Cys
               455                      460                      465

GAT  TTG  GCA  TTT  GGC  CAA  TTT  CAA  GGA  TCC  TGG  CAC  CAA  GCA  TTT  TCC     1794
Asp  Leu  Ala  Phe  Gly  Gln  Phe  Gln  Gly  Ser  Trp  His  Gln  Ala  Phe  Ser
          470                      475                      480

TTG  GGT  GTT  TGT  TCG  ACT  AAT  GTA  AAG  GGG  ATG  AAT  ATT  GTT  GTT  GCT     1842
Leu  Gly  Val  Cys  Ser  Thr  Asn  Val  Lys  Gly  Met  Asn  Ile  Val  Val  Ala
     485                      490                      495

TCA  ACA  AAG  AAT  GTT  GTT  GGT  AGT  CAA  GAA  TCT  CTC  GAA  GAG  CTT  TGC     1890
Ser  Thr  Lys  Asn  Val  Val  Gly  Ser  Gln  Glu  Ser  Leu  Glu  Glu  Leu  Cys
500                      505                      510                      515

TCC  ATT  TAC  AAA  GCT  CTC  CTT  TTA  GGC  CCT  TAGATCTCAC  ATGATGCTTG            1940
Ser  Ile  Tyr  Lys  Ala  Leu  Leu  Leu  Gly  Pro
               520                      525

ACTGATATTA  TTCGACAATA  TGATTATGTC  GTGT                                            1974
```

( 2 ) INFORMATION FOR SEQ ID NO:17:

( i ) SEQUENCE CHARACTERISTICS:
    ( A ) LENGTH: 525 amino acids
    ( B ) TYPE: amino acid
    ( D ) TOPOLOGY: linear ( i i ) MOLECULE TYPE: protein ( x i ) SEQUENCE DESCRIPTION: SEQ ID NO:17:

```
Met  Asn  Glu  Ile  Asp  Glu  Lys  Asn  Gln  Ala  Pro  Val  Gln  Gln  Glu  Cys
1                   5                        10                      15

Leu  Lys  Glu  Met  Ile  Gln  Asn  Gly  His  Ala  Arg  Arg  Met  Gly  Ser  Val
               20                      25                      30

Glu  Asp  Leu  Tyr  Val  Ala  Leu  Asn  Arg  Gln  Asn  Leu  Tyr  Arg  Asn  Phe
```

```
                    35                        40                           45
Cys  Thr  Tyr  Gly  Glu  Leu  Ser  Asp  Tyr  Cys  Thr  Arg  Asp  Gln  Leu  Thr
          50                    55                      60

Leu  Ala  Leu  Arg  Glu  Ile  Cys  Leu  Lys  Asn  Pro  Thr  Leu  Leu  His  Ile
65                       70                       75                          80

Val  Leu  Pro  Thr  Arg  Trp  Pro  Asn  His  Glu  Asn  Tyr  Tyr  Arg  Ser  Ser
                    85                       90                          95

Glu  Tyr  Tyr  Ser  Arg  Pro  His  Pro  Val  His  Asp  Tyr  Ile  Ser  Val  Leu
                    100                      105                      110

Gln  Glu  Leu  Lys  Leu  Ser  Gly  Val  Val  Leu  Asn  Glu  Gln  Pro  Glu  Tyr
               115                      120                      125

Ser  Ala  Val  Met  Lys  Gln  Ile  Leu  Glu  Glu  Phe  Lys  Asn  Ser  Lys  Gly
          130                      135                      140

Ser  Tyr  Thr  Ala  Lys  Ile  Phe  Lys  Leu  Thr  Thr  Thr  Leu  Thr  Ile  Pro
145                           150                     155                     160

Tyr  Phe  Gly  Pro  Thr  Gly  Pro  Ser  Trp  Arg  Leu  Ile  Cys  Leu  Pro  Glu
                    165                      170                      175

Glu  His  Thr  Glu  Lys  Trp  Arg  Lys  Phe  Ile  Phe  Val  Ser  Asn  His  Cys
               180                      185                      190

Met  Ser  Asp  Gly  Arg  Ser  Ser  Ile  His  Phe  Phe  His  Asp  Leu  Arg  Asp
          195                      200                      205

Glu  Leu  Asn  Asn  Ile  Lys  Thr  Pro  Pro  Lys  Lys  Leu  Asp  Tyr  Ile  Phe
     210                      215                      220

Lys  Tyr  Glu  Glu  Asp  Tyr  Gln  Leu  Leu  Arg  Lys  Leu  Pro  Glu  Pro  Ile
225                      230                      235                          240

Glu  Lys  Val  Ile  Asp  Phe  Arg  Pro  Pro  Tyr  Leu  Phe  Ile  Pro  Lys  Ser
                    245                      250                      255

Leu  Leu  Ser  Gly  Phe  Ile  Tyr  Asn  His  Leu  Arg  Phe  Ser  Lys  Gly
                    260                      265                      270

Val  Cys  Met  Arg  Met  Asp  Asp  Val  Glu  Lys  Thr  Asp  Asp  Val  Val  Thr
          275                      280                      285

Glu  Ile  Ile  Asn  Ile  Ser  Pro  Thr  Glu  Phe  Gln  Ala  Ile  Lys  Ala  Asn
     290                      295                      300

Ile  Lys  Ser  Asn  Ile  Gln  Gly  Lys  Cys  Thr  Ile  Thr  Pro  Phe  Leu  His
305                      310                      315                          320

Val  Cys  Trp  Phe  Val  Ser  Leu  His  Lys  Trp  Gly  Lys  Phe  Phe  Lys  Pro
                    325                      330                          335

Leu  Asn  Phe  Glu  Trp  Leu  Thr  Asp  Ile  Phe  Ile  Pro  Ala  Asp  Cys  Arg
               340                      345                      350

Ser  Gln  Leu  Pro  Asp  Asp  Asp  Glu  Met  Arg  Gln  Met  Tyr  Arg  Tyr  Gly
          355                      360                      365

Ala  Asn  Val  Gly  Phe  Ile  Asp  Phe  Thr  Pro  Trp  Ile  Ser  Glu  Phe  Asp
     370                      375                      380

Met  Asn  Asp  Asn  Lys  Glu  Asn  Phe  Trp  Pro  Leu  Ile  Glu  His  Tyr  His
385                      390                      395                          400

Glu  Val  Ile  Ser  Glu  Ala  Leu  Arg  Asn  Lys  Lys  His  Leu  His  Gly  Leu
                    405                      410                      415

Gly  Phe  Asn  Ile  Gln  Gly  Phe  Val  Gln  Lys  Tyr  Val  Asn  Ile  Asp  Lys
               420                      425                      430

Val  Met  Cys  Asp  Arg  Ala  Ile  Gly  Lys  Arg  Arg  Gly  Gly  Thr  Leu  Leu
          435                      440                      445

Ser  Asn  Val  Gly  Leu  Phe  Asn  Gln  Leu  Glu  Glu  Pro  Asp  Ala  Lys  Tyr
          450                      455                      460
```

```
Ser  Ile  Cys  Asp  Leu  Ala  Phe  Gly  Gln  Phe  Gln  Gly  Ser  Trp  His  Gln
465                 470                 475                 480

Ala  Phe  Ser  Leu  Gly  Val  Cys  Ser  Thr  Asn  Val  Lys  Gly  Met  Asn  Ile
                485                 490                 495

Val  Val  Ala  Ser  Thr  Lys  Asn  Val  Val  Gly  Ser  Gln  Glu  Ser  Leu  Glu
               500                 505                 510

Glu  Leu  Cys  Ser  Ile  Tyr  Lys  Ala  Leu  Leu  Leu  Gly  Pro
               515                 520                 525
```

( 2 ) INFORMATION FOR SEQ ID NO:18:

( i ) SEQUENCE CHARACTERISTICS:
        ( A ) LENGTH: 2080 base pairs
        ( B ) TYPE: nucleic acid
        ( C ) STRANDEDNESS: double
        ( D ) TOPOLOGY: linear ( i x ) FEATURE:
        ( A ) NAME/KEY: CDS
        ( B ) LOCATION: 311..1888

( x i ) SEQUENCE DESCRIPTION: SEQ ID NO:18:

```
CTTGAACATT  GATCAATGTG  AAATACTGAT  TGTGATGTTC  AATATATTTG  CTGATCTTAG        60

GGTGATTGGT  AACCAAAAAT  GCCGTCGGGC  ATTGTTCTAA  AGGCTTGTGA  TTTTGTAAGT       120

TTTTGATCG   CCTATTGTTT  TTGGGCTGGC  ATCAGCATCG  CGTGGAGCGA  AGTCCAAATA       180

TGTTTTCTAT  TGTTTTTCAT  GGCTCTTCGA  GAAGCGTCTT  TTTTAAAGCC  AACCCAACAA       240

AACTTGAGAC  ATGGAAACAG  AAGAAAGCCA  ATTTAGCAGT  ATAACAAAAA  TCATCAATCC       300

AAAAACTCTA  ATG  AAT  ACC  TAC  AGT  GAA  AAA  ACG  TCT  CTT  GTT  CAA  GAT  349
            Met  Asn  Thr  Tyr  Ser  Glu  Lys  Thr  Ser  Leu  Val  Gln  Asp
             1                  5                      10

GAA  TGT  CTT  GTC  AAG  ATG  ATA  CAG  AAT  GGG  CAT  TCC  CGG  CGT  ATG  GGA  397
Glu  Cys  Leu  Val  Lys  Met  Ile  Gln  Asn  Gly  His  Ser  Arg  Arg  Met  Gly
      15                  20                      25

TCT  GTG  GAA  GAT  TTG  TAC  GCT  GCA  CTC  AAC  AGA  CAG  AAA  TTG  TAT  CGG  445
Ser  Val  Glu  Asp  Leu  Tyr  Ala  Ala  Leu  Asn  Arg  Gln  Lys  Leu  Tyr  Arg
 30                  35                      40                          45

AAT  TTT  TCG  ACA  TAT  TCA  GAG  CTG  AAT  GAT  TAC  TGT  ACC  AAA  GAT  CAG  493
Asn  Phe  Ser  Thr  Tyr  Ser  Glu  Leu  Asn  Asp  Tyr  Cys  Thr  Lys  Asp  Gln
                50                      55                      60

CTC  GCA  TTA  GCT  CTA  AGA  AAT  ATA  TGT  TTG  AAA  AAT  CCG  ACT  CTC  CTA  541
Leu  Ala  Leu  Ala  Leu  Arg  Asn  Ile  Cys  Leu  Lys  Asn  Pro  Thr  Leu  Leu
            65                      70                      75

CAT  ATT  GTA  TTA  CCG  GCA  AGA  TGG  CCA  GAT  CAT  GAA  AAG  TAT  TAC  CTT  589
His  Ile  Val  Leu  Pro  Ala  Arg  Trp  Pro  Asp  His  Glu  Lys  Tyr  Tyr  Leu
            80                      85                      90

AGC  TCA  GAA  TAT  TAT  TCA  CAG  CCC  CGT  CCA  AAA  CAT  GAT  TAT  ATT  TCG  637
Ser  Ser  Glu  Tyr  Tyr  Ser  Gln  Pro  Arg  Pro  Lys  His  Asp  Tyr  Ile  Ser
      95                      100                     105

GTT  TTG  CCT  GAG  TTG  AAA  TTA  GAT  GGT  GTG  ATT  CTC  AAC  GAG  CAA  CCT  685
Val  Leu  Pro  Glu  Leu  Lys  Leu  Asp  Gly  Val  Ile  Leu  Asn  Glu  Gln  Pro
110                      115                     120                     125

GAG  CAC  AAT  GCC  CTA  ATG  AAG  CAA  ATA  CTA  GAA  GAA  TTT  GCG  AAT  AGC  733
Glu  His  Asn  Ala  Leu  Met  Lys  Gln  Ile  Leu  Glu  Glu  Phe  Ala  Asn  Ser
                130                     135                     140

AAT  GGA  TCT  TAT  ACT  GCA  AAA  ATC  TTT  AAA  TTG  ACC  ACC  GCT  TTG  ACT  781
Asn  Gly  Ser  Tyr  Thr  Ala  Lys  Ile  Phe  Lys  Leu  Thr  Thr  Ala  Leu  Thr
            145                     150                     155

ATA  CCT  TAC  ACT  GGG  CCA  ACA  AGT  CCA  ACT  TGG  CGG  TTG  ATT  TGT  CTC  829
Ile  Pro  Tyr  Thr  Gly  Pro  Thr  Ser  Pro  Thr  Trp  Arg  Leu  Ile  Cys  Leu
            160                     165                     170
```

| | | | | | | | | | | | | | | | | |
|---|---|---|---|---|---|---|---|---|---|---|---|---|---|---|---|---|
| CCA | GAA | GAA | GAT | GAC | ACG | AAT | AAG | TGG | AAG | AAA | TTT | ATA | TTT | GTA | TCC | 877 |
| Pro | Glu | Glu | Asp | Asp | Thr | Asn | Lys | Trp | Lys | Lys | Phe | Ile | Phe | Val | Ser | |
| | 175 | | | | 180 | | | | | 185 | | | | | | |
| AAT | CAC | TGC | ATG | TGC | GAT | GGT | AGA | TCC | TCA | ATT | CAC | TTT | TTT | CAG | GAT | 925 |
| Asn | His | Cys | Met | Cys | Asp | Gly | Arg | Ser | Ser | Ile | His | Phe | Phe | Gln | Asp | |
| 190 | | | | | 195 | | | | | 200 | | | | | 205 | |
| CTA | AGA | GAT | GAA | TTA | AAC | AAC | ATA | AAA | ACT | CTG | CCA | AAG | AAA | TTG | GAC | 973 |
| Leu | Arg | Asp | Glu | Leu | Asn | Asn | Ile | Lys | Thr | Leu | Pro | Lys | Lys | Leu | Asp | |
| | | | | 210 | | | | | 215 | | | | | 220 | | |
| TAC | ATT | TTC | GAG | TAC | GAA | AAG | GAT | TAC | CAA | CTT | TTG | AGA | AAG | CTC | CCA | 1021 |
| Tyr | Ile | Phe | Glu | Tyr | Glu | Lys | Asp | Tyr | Gln | Leu | Leu | Arg | Lys | Leu | Pro | |
| | | | 225 | | | | | 230 | | | | | 235 | | | |
| GAA | CCC | ATT | GAA | AAT | ATG | ATA | GAT | TTC | AGG | CCG | CCA | TAT | TTG | TTT | ATT | 1069 |
| Glu | Pro | Ile | Glu | Asn | Met | Ile | Asp | Phe | Arg | Pro | Pro | Tyr | Leu | Phe | Ile | |
| | | 240 | | | | | 245 | | | | | 250 | | | | |
| CCG | AAG | TCT | CTT | CTT | TCT | GGT | TTT | ATT | TAC | AGT | CAT | TTG | AGG | TTT | TCT | 1117 |
| Pro | Lys | Ser | Leu | Leu | Ser | Gly | Phe | Ile | Tyr | Ser | His | Leu | Arg | Phe | Ser | |
| | 255 | | | | | 260 | | | | | 265 | | | | | |
| TCA | AAG | GGT | GTT | TGC | ACG | AGA | ATG | GAT | GAG | ATA | GAA | AAA | AGT | GAT | GAG | 1165 |
| Ser | Lys | Gly | Val | Cys | Thr | Arg | Met | Asp | Glu | Ile | Glu | Lys | Ser | Asp | Glu | |
| 270 | | | | | 275 | | | | | 280 | | | | | 285 | |
| ATT | GTT | ACA | GAA | ATT | ATC | AAT | ATT | TCT | CCA | TCA | GAG | TTT | CAA | AAA | ATT | 1213 |
| Ile | Val | Thr | Glu | Ile | Ile | Asn | Ile | Ser | Pro | Ser | Glu | Phe | Gln | Lys | Ile | |
| | | | | 290 | | | | | 295 | | | | | 300 | | |
| AGA | ACG | AAA | ATT | AAA | TTA | AAC | ATT | CCC | GGT | AAG | TGC | ACC | ATC | ACT | CCG | 1261 |
| Arg | Thr | Lys | Ile | Lys | Leu | Asn | Ile | Pro | Gly | Lys | Cys | Thr | Ile | Thr | Pro | |
| | | | 305 | | | | | 310 | | | | | 315 | | | |
| TTC | TTA | GAA | GTT | TGT | TGG | TTT | GTT | ACT | CTC | CAT | AAA | TGG | GGC | AAG | TTT | 1309 |
| Phe | Leu | Glu | Val | Cys | Trp | Phe | Val | Thr | Leu | His | Lys | Trp | Gly | Lys | Phe | |
| | | 320 | | | | | 325 | | | | | 330 | | | | |
| TTC | AAA | CCA | CTG | AAG | TTC | GAG | TGG | CTC | ACT | GAT | GTT | TTT | ATA | CCT | GCA | 1357 |
| Phe | Lys | Pro | Leu | Lys | Phe | Glu | Trp | Leu | Thr | Asp | Val | Phe | Ile | Pro | Ala | |
| | 335 | | | | | 340 | | | | | 345 | | | | | |
| GAT | TGC | CGC | TCA | TTG | CTG | CCT | GAA | GAT | GAA | GAA | GTG | AGA | GCT | ATG | TAC | 1405 |
| Asp | Cys | Arg | Ser | Leu | Leu | Pro | Glu | Asp | Glu | Glu | Val | Arg | Ala | Met | Tyr | |
| 350 | | | | | 355 | | | | | 360 | | | | | 365 | |
| AGG | TAC | GGC | GCT | AAC | GTT | GGG | TTT | GTT | GAC | TTC | ACT | CCA | TGG | ATA | AGC | 1453 |
| Arg | Tyr | Gly | Ala | Asn | Val | Gly | Phe | Val | Asp | Phe | Thr | Pro | Trp | Ile | Ser | |
| | | | | 370 | | | | | 375 | | | | | 380 | | |
| AAA | TTC | AAC | ATG | AAC | GAC | AGC | AAA | GAA | AAT | TTC | TGG | CCA | CTT | ATT | GCA | 1501 |
| Lys | Phe | Asn | Met | Asn | Asp | Ser | Lys | Glu | Asn | Phe | Trp | Pro | Leu | Ile | Ala | |
| | | | 385 | | | | | 390 | | | | | 395 | | | |
| CAT | TAT | CAT | GAA | GTA | ATT | TCC | GGG | GCG | ATA | AAA | GAC | AAG | AAG | CAT | CTC | 1549 |
| His | Tyr | His | Glu | Val | Ile | Ser | Gly | Ala | Ile | Lys | Asp | Lys | Lys | His | Leu | |
| | | 400 | | | | | 405 | | | | | 410 | | | | |
| AAT | GGT | TTG | GGG | TTC | AAC | ATA | CAA | AGC | TTG | GTC | CAA | AAG | TAT | GTC | AAC | 1597 |
| Asn | Gly | Leu | Gly | Phe | Asn | Ile | Gln | Ser | Leu | Val | Gln | Lys | Tyr | Val | Asn | |
| | 415 | | | | | 420 | | | | | 425 | | | | | |
| ATT | GAT | AAA | GTA | ATG | CGT | GAT | CGT | GCT | CTT | GGT | AAA | TCA | CGT | GGG | GGC | 1645 |
| Ile | Asp | Lys | Val | Met | Arg | Asp | Arg | Ala | Leu | Gly | Lys | Ser | Arg | Gly | Gly | |
| 430 | | | | | 435 | | | | | 440 | | | | | 445 | |
| ACT | TTG | TTG | AGC | AAC | GTA | GGT | ATG | TTC | CAC | CAA | TCG | GAG | GAG | ACC | GAA | 1693 |
| Thr | Leu | Leu | Ser | Asn | Val | Gly | Met | Phe | His | Gln | Ser | Glu | Glu | Thr | Glu | |
| | | | | 450 | | | | | 455 | | | | | 460 | | |
| CAC | AAG | TAT | CGT | ATA | AGA | GAT | TTG | GCC | TTT | GGT | CAA | TTT | CAA | GGG | TCA | 1741 |
| His | Lys | Tyr | Arg | Ile | Arg | Asp | Leu | Ala | Phe | Gly | Gln | Phe | Gln | Gly | Ser | |
| | | | 465 | | | | | 470 | | | | | 475 | | | |
| TGG | CAT | CAA | GCT | TTT | TCA | TTG | GGT | GTT | TCT | TCG | ACT | AAT | GTG | AAG | GGA | 1789 |
| Trp | His | Gln | Ala | Phe | Ser | Leu | Gly | Val | Ser | Ser | Thr | Asn | Val | Lys | Gly | |
| | | 480 | | | | | 485 | | | | | 490 | | | | |

```
ATG AAC ATT TTG ATT TCT TCA ACG AAA AAT GTC GTG GGT AGT CAA GAA         1837
Met Asn Ile Leu Ile Ser Ser Thr Lys Asn Val Val Gly Ser Gln Glu
    495                 500                 505

TTG TTG GAG GAA CTT TGT GCT ATG TAC AAG GCT CTG CTT TTA AAT CCC         1885
Leu Leu Glu Glu Leu Cys Ala Met Tyr Lys Ala Leu Leu Leu Asn Pro
510                 515                 520                 525

TGATTCTTCT AAGACAATAT GATGGTGGAT ACCTTAAAA ATTATAGTTA TATTGTAGGG        1945

CTATCCTGTT TTGATATTAT AATGTTTTTT TAGCTTGTAG AGAGAAATGG TATCAGTTTC        2005

TTTTACTAAG ATTCGAACTA ATCAATATCT CAAAGTGATT AAACGACGTG TGTAAGGTAA       2065

GTAAGTGTAC AGAAA                                                        2080
```

( 2 ) INFORMATION FOR SEQ ID NO:19:

( i ) SEQUENCE CHARACTERISTICS:
        ( A ) LENGTH: 525 amino acids
        ( B ) TYPE: amino acid
        ( D ) TOPOLOGY: linear ( i i ) MOLECULE TYPE: protein ( x i ) SEQUENCE DESCRIPTION: SEQ ID NO:19:

```
Met Asn Thr Tyr Ser Glu Lys Thr Ser Leu Val Gln Asp Glu Cys Leu
 1               5                  10                  15

Val Lys Met Ile Gln Asn Gly His Ser Arg Arg Met Gly Ser Val Glu
             20                  25                  30

Asp Leu Tyr Ala Ala Leu Asn Arg Gln Lys Leu Tyr Arg Asn Phe Ser
             35                  40                  45

Thr Tyr Ser Glu Leu Asn Asp Tyr Cys Thr Lys Asp Gln Leu Ala Leu
     50                  55                  60

Ala Leu Arg Asn Ile Cys Leu Lys Asn Pro Thr Leu Leu His Ile Val
65                  70                  75                  80

Leu Pro Ala Arg Trp Pro Asp His Glu Lys Tyr Tyr Leu Ser Ser Glu
                 85                  90                  95

Tyr Tyr Ser Gln Pro Arg Pro Lys His Asp Tyr Ile Ser Val Leu Pro
             100                 105                 110

Glu Leu Lys Leu Asp Gly Val Ile Leu Asn Glu Gln Pro Glu His Asn
         115                 120                 125

Ala Leu Met Lys Gln Ile Leu Glu Glu Phe Ala Asn Ser Asn Gly Ser
     130                 135                 140

Tyr Thr Ala Lys Ile Phe Lys Leu Thr Thr Ala Leu Thr Ile Pro Tyr
145                 150                 155                 160

Thr Gly Pro Thr Ser Pro Thr Trp Arg Leu Ile Cys Leu Pro Glu Glu
                 165                 170                 175

Asp Asp Thr Asn Lys Trp Lys Lys Phe Ile Phe Val Ser Asn His Cys
             180                 185                 190

Met Cys Asp Gly Arg Ser Ser Ile His Phe Phe Gln Asp Leu Arg Asp
         195                 200                 205

Glu Leu Asn Asn Ile Lys Thr Leu Pro Lys Lys Leu Asp Tyr Ile Phe
     210                 215                 220

Glu Tyr Glu Lys Asp Tyr Gln Leu Leu Arg Lys Leu Pro Glu Pro Ile
225                 230                 235                 240

Glu Asn Met Ile Asp Phe Arg Pro Pro Tyr Leu Phe Ile Pro Lys Ser
                 245                 250                 255

Leu Leu Ser Gly Phe Ile Tyr Ser His Leu Arg Phe Ser Ser Lys Gly
             260                 265                 270
```

-continued

```
Val Cys Thr Arg Met Asp Glu Ile Glu Lys Ser Asp Glu Ile Val Thr
        275             280              285
Glu Ile Ile Asn Ile Ser Pro Ser Glu Phe Gln Lys Ile Arg Thr Lys
    290             295              300
Ile Lys Leu Asn Ile Pro Gly Lys Cys Thr Ile Thr Pro Phe Leu Glu
305             310              315                      320
Val Cys Trp Phe Val Thr Leu His Lys Trp Gly Lys Phe Phe Lys Pro
            325              330              335
Leu Lys Phe Glu Trp Leu Thr Asp Val Phe Ile Pro Ala Asp Cys Arg
            340              345              350
Ser Leu Leu Pro Glu Asp Glu Val Arg Ala Met Tyr Arg Tyr Gly
        355             360              365
Ala Asn Val Gly Phe Val Asp Phe Thr Pro Trp Ile Ser Lys Phe Asn
    370              375             380
Met Asn Asp Ser Lys Glu Asn Phe Trp Pro Leu Ile Ala His Tyr His
385             390              395                      400
Glu Val Ile Ser Gly Ala Ile Lys Asp Lys Lys His Leu Asn Gly Leu
            405             410               415
Gly Phe Asn Ile Gln Ser Leu Val Gln Lys Tyr Val Asn Ile Asp Lys
            420             425              430
Val Met Arg Asp Arg Ala Leu Gly Lys Ser Arg Gly Gly Thr Leu Leu
        435             440              445
Ser Asn Val Gly Met Phe His Gln Ser Glu Glu Thr Glu His Lys Tyr
    450             455              460
Arg Ile Arg Asp Leu Ala Phe Gly Gln Phe Gln Gly Ser Trp His Gln
465             470              475                      480
Ala Phe Ser Leu Gly Val Ser Ser Thr Asn Val Lys Gly Met Asn Ile
            485             490              495
Leu Ile Ser Ser Thr Lys Asn Val Val Gly Ser Gln Glu Leu Leu Glu
            500             505              510
Glu Leu Cys Ala Met Tyr Lys Ala Leu Leu Leu Asn Pro
            515             520              525
```

ALCOHOL ACETYLTRANSFERASE GENES AND USE THEREOF

This application is a divisional of application Ser. No. 08/077,939, filed on Jun. 18, 1993, now U.S. Pat. No. 5,521,088, issued May 28, 1996.

BACKGROUND OF THE INVENTION

1. Field of the Invention

The present invention relates to an alcohol acetyltransferase ("AATase") produced by, for example, *Saccharomyces cerevisiae*, a DNA sequence encoding, i.e., having an ability for biotechnologically producing, AATase, and a yeast having an improved ester producing ability due to the transformation with the DNA sequence. The present invention also relates to a process for producing an alcoholic beverage having an enhanced ester flavor.

2. Related Art

It is well known that acetate esters affect the flavor quality of alcoholic beverages such as sake, beer, wine and whisky. These esters are in general present in the fermented supernatant, because yeast produces a various kinds of alcohols which are further converted into esters during a fermentation procedure.

In particular, isoamyl acetate is an ester which provides a good fruity flavor for alcoholic beverages. It has been suggested that the ratio of isomyl acetate to isoamyl alcohol, which is a precursor of isomyl acetate, is closely related to the evaluation value of the sensary test. For example, sake having a great ratio of isomyl acetate to isoamyl alcohol valued as "Ginjo-shu" in the sensary test (JOHSHI HOKOKU, No. 145, P. 26 (1973)).

AS previously reported by Yoshioka et al., Agric. Biol. Chem., 45, 2188 (1981), AATase is an enzyme which plays primary role in the production of isoamyl acetate. The AATase synthesizes isoamyl acetate by the condensation of isoamyl alcohol and acetyl-CoA. Furthermore, AATase has been known to have a wide substrate specificity and to produce many acetate esters such as ethyl acetate in the same mechanism as described above.

Therefore, in order to increase the esters, such as isoamyl acetate in the alcoholic beverages, it is effective to enhance the AATase activity of a yeast. Some of the conventional consideration in the production of the alcoholic beverages, for example, selecting raw materials or controlling fermentation conditions, as a result, have enhanced the activity of the AATase.

However, though it has been well known that AATase is important enzyme for the production of esters, there are few reports referring to the AATase. Partial purifications of the enzyme have been described in some reports (for example, NIPPON NOGEI KAGAKUKAISHI, 63, 435 (1989); Agric. Biol. Chem., 54, 1485 (1990); NIPPON JOZO KYOKAISHI, 87, 334 (1992)), but, because AATase has very labile activity, complete purification of AATase, and the cloning of the gene encoding AATase has not been reported, so far.

SUMMARY OF THE INVENTION

An object of the present invention is to reveal the structure of AATase and isolate the AATase gene, thereby to obtain a transformed yeast having an enhanced AATase producing ability and to produce an alcoholic beverage having an enhanced ester flavor.

According to the first embodiment of the present invention, the present invention provides an AATase originated from yeast having an ability for transferring the acetyl group from acetyl-CoA to an alcohol to produce an acetate ester and having a molecular weight of approximately 60,000 by SDS-PAGE.

According to the second embodiment of the present invention, the present invention provides an AATase comprising a polypeptide selected from a group consisting of:

(1a) a polypeptide having an amino acid sequence from A to B of the amino acid sequence (SEQ ID NO:15) shown in FIG. 1;

(1b) a polypeptide having an amino acid sequence from A to B of the amino acid sequence (SEQ ID NO:17) shown in FIG. 2; and (1c) a polypeptide having an amino acid sequence from A to C or B to C (SEQ ID NO:19 or residues 19-525 of SEQ ID NO:19) of the amino acid sequence shown in FIG. 17.

According to the third embodiment of the present invention, the present invention provides the AATase encoding gene having a DNA sequence selected from a group the consisting of:

(2a) a DNA sequence encoding a polypeptide having an amino acid sequence from A to B of the amino acid sequence (SEQ ID NO:15) shown in FIG. 1;

(2b) a DNA sequence encoding a polypeptide having an amino acid sequence from A to B of the amino acid sequence (SEQ ID NO:17) shown in FIG. 2; and (2c) a DNA sequence encoding a polypeptide having an amino acid sequence from A to C or B to C (SEQ ID NO:19 or residues 19-525 of SEQ ID NO:19) of the amino acid sequence shown in FIG. 17.

According to the fourth embodiment of the present invention, the present invention provides a DNA sequence comprising an AATase gene selected from a group consisting of:

(3a) an AATase gene having a DNA sequence from A to B (bases 233-1808 of SEQ ID NO:14) of the DNA sequence shown in FIG. 1;

(3b) an AATase gene having a DNA sequence from A to B (bases 346-11920 of SEQ ID NO:16) of the DNA sequence shown in FIG. 2;

(3c) an AATase gene having a DNA sequence from A to C or B to C (bases 311-1885 or 365-1885 of SEQ ID NO:18) of the DNA sequence shown in FIG. 17; and (3d) a DNA sequence which hybridizes with any one of genes (3a) to (3c).

According to the fifth embodiment of the present invention, the present invention provides a transformed yeast having an enhanced AATase producing ability due to the transformation using the AATase gene selected from (2a) to (2c) or a DNA sequence selected from (3a) to (3d).

According to the sixth embodiment of the present invention, the present invention provides a process for producing a alcoholic beverage having an enriched ester flavor using a transformed yeast as described above.

According to the seventh embodiment of the present invention, the present invention provides a method for isolating a DNA sequence encoding AATase, comprising the steps of:

(a) preparing a DNA fragment having a length of at least 20 bases of a DNA sequence which encodes a polypeptide having an amino acid sequence from A to B (SEQ ID NO:15) of the amino acid sequence shown in FIG. 1;

(b) preparing a gene library which has been made from DNA strands having a substantially same length in the range from 5×10³ to 30×10³ bases obtained by cutting the chromosome of a yeast;

(c) cloning a DNA fragment by hybridization from gene library of (b), using the DNA fragment of (a) as a probe.

The terms "DNA fragment", "DNA sequence" and "gene" are herein intended to be substantially synonymously.

Since the AATase gene have been obtained, a yeast can be transformed using this gene as a foreign gene by a genetic engineering method. That is, the gene can be transfected into a yeast cell as a extranuclear and/or intranuclear gene to afford the yeast an AATase producing ability greater than that of the host cell, and using these transformants an alcoholic beverage having the enriched ester flavor can be made.

BRIEF DESCRIPTION OF THE DRAWINGS

FIGS. 1(a) through 1(f) show an amino acid sequence (SEQ ID NO:15) of AATase and DNA sequence (SEQ ID NO:14) of the AATase encoding gene according to the present invention;

FIGS. 2 (a) through 2 (f) show a amino acid sequence (SEQ ID NO:17) of AATase and DNA sequence (SEQ ID NO:16) of another AATase encoding gene according to the present invention;

FIG. 3 shows a restriction map of the AATase encoding gene originated from a sake yeast according to the present invention;

FIG. 7 shows the elution profile of an AATase active fraction by the affinity chromatography method among the purification processes according to the present invention;

FIGS. 17(a) through 17(f) shows the amino acids (SEQ ID NO:19) and DNA sequence (SEQ ID NO:18) of the brewery lager yeast AATase 2 gene according to the present invention.

DETAILED DESCRIPTION OF THE INVENTION

AATase

Figure 4:
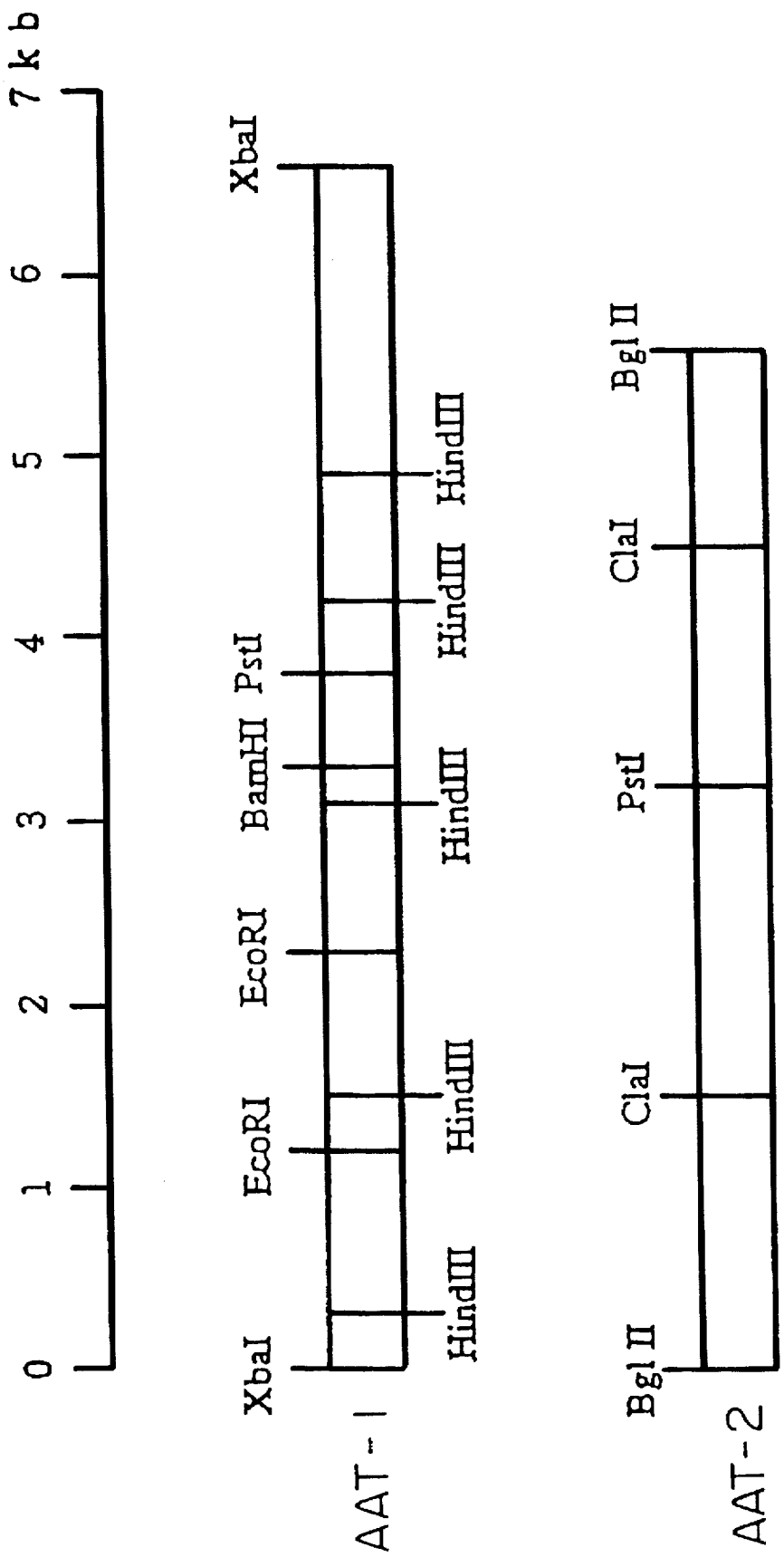
FIG. 4 shows two restriction maps of the AATase originated from a brewery lager yeast according to the present invention.

AATase, alcohol acetyltransferase, is an enzyme having an ability for producing an acetate ester by transferring the acetyl group from acetyl-CoA to alcohols.

The alcohols herein primarily mean alcohols having straight or branched chains having 1 to 6 carbon atoms. According to our studies, however, it has been found that the AATase may employ as substrates alcohols having a higher number of carbon atoms such as 2-phenyl ethylalcohol.

Thus, "the alcohols" should be construed to include a wide range of alcohols, if it is necessary to discuss the substrate alcohol of the AATase in the present invention.

The AATase according to the present invention is originated from yeast. The AATase is specifically obtained from Saccharomyces cerevisiae and is a polypeptide having any one of the polypeptides (1a)–(1c) defined above. Specifically, the polypeptide includes a polypeptide having an amino acid sequence from A to B (SEQ ID NO:15) of the amino acid sequence shown in FIGS. 1(a) through 1(f); a polypeptide having an amino acid sequence from A to B (SEQ ID NO:17) of the amino acid sequence shown in FIGS. 2(a) through 2(f); a polypeptide having an amino acid sequence from A to C (SEQ ID NO:19) of the amino acid sequence shown in FIGS. 17(a) through 17(f); and a polypeptide having an amino acid sequence from B to C (residues 19-525 of SEQ ID NO:19) of the amino acid sequence shown in FIGS. 17(a) through 17(f). Furthermore, it has been clarified by genetic engineering or protein engineering that the physiological activity of a polypeptide may be maintained with the addition, insertion, elimination, deletion or substitution of one or more of the amino acids of the polypeptide. The polypeptide therefore include a modified polypeptide of any one of the above polypeptides due to the addition, insertion, elimination, deletion or substitution of one or more of amino acid of the polypeptide so long as the modified polypeptide has an AATase activity.

Saccharomyces cerevisiae used herein is a microorganism described in "The yeast, a taxonomic study", the 3rd Edition, (ed. by N. J. W. Kreger-van Rij, Elsevier Publishers B.V., Amsterdam (1984), page 379), or a synonym or mutant thereof.

AATase and its purification method have been reported in some papers, for instance, NIPPON NOGEIKAGAKU KAISHI, 63, 435 (1989); Agric. Biol. Chem., 54, 1485 (1990); NIPPON JOSO KYOKAISHI, 87, 334 (1992). However, so far as the present inventors know, the AATase has not been purified to homogeneity, so its amino acid sequence has not been determined.

The present inventors have now found that an affinity column with 1-hexanol as a ligand can be used successfully for purifying the AATase. We have thus completely purified the AATase from Saccharomyces cerevisiae by use of this affinity column and defined some properties of the enzyme. The amino acid sequence shown in FIGS. 1(a) through 1(f) (SEQ ID NO:19) is obtained by analysis of the AATase originated from Saccharomyces cerevisiae which has thus purified to homogeneity.

The typical property of the AATase which have been defined according to the present invention includes the molecular weight of the AATase. Although the molecular weight of the AATase previously reported is in the range from 45,000 to 56,000, the molecular weight of the AATase purified according to the present invention is approximately 60,000 by SDS-polyacrylamide gel electrophoresis (SDS-PAGE), suggesting that it is different from the protein reported previously. The molecular weight of the AATase deduced from the DNA sequence was ca. 61,000.

The AATase of the present invention has enzymological and physicochemical properties as set forth below.

(a) Action

This enzyme acts on a variety of alcohol such as ethyl alcohol and acetyl-CoA to produce an acetate ester.

(b) Substrate specificity

This enzyme acts on various kinds of alcohol having 2 to 5 carbon atoms, more efficiently on alcohols having 2 to 5 carbon atoms. In addition, the enzyme acts more efficiently on straight chain alcohols rather branched chain alcohols.

(c) Molecular weight: ca. 60,000

(d) Optimum and stable pH:
optimum pH: 8.0,
stable pH: 7.5 –8.5

(e) Optimum and stable temperature:
optimum temperature: 25° C.,
stable temperature: 4° C.;

(f) Inhibitors:

This enzyme is intensively inhibited by parachloromercury benzoate (PCMB) and dithiobisbenzoic acid (DTNB);

(g) Effects of various fatty acids on the activity:

This enzyme is not noticeably inhibited by a saturated fatty acid but intensively inhibited by an unsaturated fatty acid;

(h) Km value to isoamyl alcohol and acetyl-CoA:
isoamyl alcohol: 29.8 mM, acetyl CoA: 190 µM.

The AATase can be obtained by a procedure comprising culturing yeast cells of *Saccharomyces cerevisiae* KYOKAI No. 7 and recovering and purifying the crude enzyme from the content of the organism as described in Examples below.

DNA sequence or DNA fragment/gene which produces AATase

In the present invention, the DNA sequence or DNA fragment having an ability of producing AATase means the DNA sequence or DNA fragment which codes for a polypeptide having AATase activities. The amino acid sequence of a polypeptide encoded by the sequence or fragment, i.e., the AATase, is selected from the group consisting of the following (2a)–(2c), and is specifically selected from the group consisting of the following (3a)–(3d):

(2a) a DNA sequence encoding a polypeptide having an amino acid sequence from A to B (SEQ ID NO:15) of the amino acid sequence shown in FIGS. 1(a) through 1(f);

(2b) a DNA sequence encoding a polypeptide having an amino acid sequence from A to B (SEQ ID NO:17) of the amino acid sequence shown in FIGS. 2(a) through 2(f);

(2C) a DNA sequence encoding a polypeptide having an amino acid sequence from A to C or B to C of the amino acid sequence shown in FIGS. 17(a) through 17(f).

(3a) an AATase gene having a DNA sequence from A to B (bases 233-1808 of SEQ ID NO:14) of the DNA sequence shown in FIGS. 1(a) through 1(f);

(3b) an AATase gene having a DNA sequence from A to B (bases 346-1920 of SEQ ID NO:16) of the DNA sequence shown in FIGS. 2(a) through 2(f);

(3c) an AATase gene having a DNA sequence from A to C or S to C (bases 311-1885 or 365-1885 of SEQ ID NO:18) of the DNA sequence shown in FIGS. 17(a) through 17(f); and (3d) a DNA sequence capable of hybridizing with any one of genes (3a) to (3c).

The DNA sequence varies depending upon the variation of the polypeptide. In addition, it is well known by one skilled in the art that a DNA sequence is easily defined according to the knowledge referring to the so called "degeneracy", once an amino acid sequence is given. Thus, one skilled in the art can understand that certain codons present in the sequence shown in FIGS. 1(a)–1(f), 2(a)–2(f), and 17(a)–17(f) can be substituted by other codons and produce a same polypeptide. This means that the DNA sequence (or DNA fragment) of the present invention includes DNA sequences which encode the same peptide but are different DNA sequences in which codons in the degeneracy relation are used. Furthermore, one skilled in the art can understand that the DNA sequence of the present invention include the DNA sequence which encodes a modified polypeptide of any of one of the polypeptides (1a) to (1c) due to the addition, insertion, elimination, deletion or substitution of one or more amino acid of these polypeptides. In this connection, the term "encoding" is synonymous with the term "capable of encoding".

The DNA sequence of the present invention may be obtained from a natural gene source or obtained by total synthesis or semi-synthesis (i.e., synthesized with use of a part of a DNA sequence originated from a natural gene source).

Form the natural gene source, the DNA sequence of the present invention can be obtained by conducting DNA manipulations such as plaque hybridization, colony hybridization and PCR process using a probe which is a part of a DNA sequence producing the AATase of the present invention. These methods are well-known to one skilled in the art and can be easily performed.

Suitable gene sources for obtaining a DNA sequence having an AATase producing ability by these methods include for example bacteria, yeast and plants. Among these gene sources, yeast which is currently used for the production of fermentation foods such as sake and soy sauce is one of the best candidate having a DNA sequence of the present invention.

The typical form of the DNA sequence of the present invention is a polypeptide which has a length just corresponding to the length of AATase. In addition, the DNA sequence of the present invention may have an additional DNA sequences which are bonded upstream and/or downstream the sequence. A specific example of the latter is a vector such as plasmid carrying the DNA sequence of the present invention.

Suitable example of the DNA sequence of the present invention is from A to B of the amino acid sequence shown in FIGS. 1(a) through 1(f) (bases 233-1808 of SEQ ID NO:14). This sequence is obtained by analyzing an AATase encoding gene obtained from a yeast strain, SAKE YEAST KYOKAI No. 7.

Transformation

The procedure or method for obtaining a transformant is commonly used in the field of genetic engineering. In addition to the method described below, any conventional transformation method (for example, Analytical Biochemistry, 163, 391 (1987)), is useful to obtain the transformant.

Vectors which can be used include all of the known vectors for yeast such as YRp vectors (multicopy vectors for yeast containing the ARS sequence of the yeast chromosome as a replication origin), YEp vectors (multicopy vectors for yeast containing the replication origin of the 2 µm DNA of yeast), YCp vectors (single copy vectors for yeast containing the DNA sequence of the ARS sequence of the gene chromosome and the DNA sequence of the centromere of the yeast chromosome), YIp vectors (integrating vectors for yeast having no replication origin of the yeast). These vectors is well-known and described in "Genetic Engineering for the Production of Materials", NIPPON NOGEI KAGAKUKAI ABC Series, ASAKURA SHOTEN, p.68, but also can be easily prepared.

In addition, in order to express the gene of the DNA sequence according to the present invention or to increase or decrease the expression, it is preferable that the expression vector contains a promoter which is a unit for controlling transcription and translation in the 5'-upstream region and a terminator in the 3'-downstream region of the DNA sequence. Suitable promoters and terminators are for example those originated from the AATase gene itself, those originated from any known genes such as alcohol dehydrogenase gene (J. Biol. Chem., 257, 3018 (1982)), phosphoglycerate kinase gene (Nucleic Acids Res., 10, 7791 (1982)) or glycerolaldehyde-3-phosphate dehydrogenase gene [J. Biol. Chem., 254, 9839 (1979)) or those which are the artificial modifications of the former.

The yeast to be transformed in the present invention, i.e. the host yeast, may be any yeast strain which belongs taxonomically to the category of yeast, but for the purpose of the present invention, a yeast strain for producing alcoholic beverages which belongs to *Saccharomyces cerevisiae* such as brewery yeast, sake yeast and wine yeast are preferred. Suitable examples of yeast include brewery yeast such as ATCC 26292, ATCC 2704, ATCC 32634 and AJL 2155; sake yeast such as ATCC 4134, ATCC 26421 and IFO 2347; and wine yeast such as ATCC 38637, ATCC 38638 and IFO 2260.

Another group preferred as the host yeast is baker's yeast such as ATCC 32120.

Preparation of Alcoholic Beverages

The transformed yeast having an enhanced AATase producing ability is provided with a character intrinsic to the host yeast as well as the introduced character. The transformant thus can be used for various applications focussed to the intrinsic character.

If the host yeast is a yeast for preparing alcoholic beverages, the transformed yeast also has an ability for fermenting saccharides to alcohols. Therefore, the transformed yeast according to the present invention provides an alcoholic beverages having an enhanced or enriched ester flavor.

Typical alcoholic beverages include sake, wine, whiskey and beer. In addition, the process for preparing these alcoholic beverages are well-known.

Production of Other AATases

As described above, the present invention provides the AATase gene encoding amino acid sequence from A to B of the amino acid sequence shown in (SEQ ID NO:15) FIGS. 1(a) through 1(f). According to another aspect of the present invention, the present invention provides other AATase genes. It has now been found that a different kind of AATase producing gene is obtained from a yeast gene library by use of a probe which is a relatively short DNA fragment of a DNA sequence encoding the amino acid sequence from A to B (SEQ ID NO:15) of the amino acid sequence shown in FIGS. 1(a) through 1(f). It is interesting in this case that the probe originated from the DNA sequence obtained from a "sake" yeast provided two different DNA sequences having an AATase producing ability from the gene library of a brewery lager yeast. In addition, while both of these DNA sequences are capable of producing AATase, the restriction maps, DNA sequences and the amino acid sequences of the DNA sequences are different from those of the amino acid sequence shown in (SEQ ID NO:15) FIGS. 1(a) through 1(f) originated from a sake yeast.

In the process of isolating these DNA sequences, a DNA fragment as a probe is first provided. The probe has preferably a length of at least 20 bases of the DNA sequence encoding a polypeptide having an amino acid from A to B (SEQ ID NO:15) of the amino acid sequence substantially shown in FIGS. 1(a) through 1(f).

The length of the DNA strand as the probe is preferably at least 20 bases, since sufficient hybridization will not occur with an excessively short probe. The DNA strand has more preferably a length of 100 bases or more.

The gene library to which the probe is applied preferably comprises vectors containing DNA fragments having a substantially same length in the range from $5 \times 10^3$ bases to $30 \times 10^3$ bases obtained by cutting a chromosome of yeast by chemical or physical means such as restriction enzyme or supersonic.

The restriction enzyme to be used in this procedure, of which the kinds and/or the reaction conditions should be set up so that for a certain yeast chromosome the DNA strands having a length within the above range are obtained. In case of making gene library from brewery yeast chromosommal DNA, suitable restriction enzymes include for example Sau3AI or MboI.

It is desirable that the DNA fragment obtained by cutting have substantially the same length in the range from $5 \times 10^3$ bases to $30 \times 10^3$ bases, in other words, the DNA fragment in the digested product with restriction enzyme has uniform length within the range from $5 \times 10^3$ bases to $30 \times 10^3$ bases.

Cloning of the complementary DNA strands from the gene library using probes, and the subcloning of this cloned DNA fragments, for example, into the yeast is easily performed according to the well-known genetic engineering method (for example, Molecular Cloning, Cold Spring Harbor Laboratory (1988)).

The amino acid sequence shown in FIGS. 2(a) through 2(f) (SEQ ID NO:17) is a polypeptide encoded by one of the two DNA sequences obtained from the brewery lager yeast gene library by using a probe which has a sequence corresponding to the DNA sequence from 234 to 1451 shown in FIGS. 1(a) through 1(f) (SEQ ID NO:14). It is apparent from comparing the figures, the AATaSes originated from brewery lager yeast and sake yeast, are different from each other only in 12 base pairs and 3 amino acids. The polypeptide having an amino acid sequence from A to B shown in FIGS. 2(a) through 2(f) (SEQ ID NO:17) which was obtained with the hybridization/cloning method described above, can also be regarded as an equivalent polypeptide of the amino acid sequence from A to B (SEQ ID NO:19) shown in FIGS. 1(a) through 1(f), i.e., as a modified polypeptide in which some of amino acids have been deleted, substituted or added.

Similarly, the amino acid sequences (from A to C or from B to C) shown in FIGS. 17(a) through 17(f) (SEQ ID NO:19 or residues 19-525 of SEQ ID NO: 19 ) is polypeptides encoded by the other DNA sequence obtained from the gene library of brewery larger yeast by using the some probe. It is apparent from comparing the figures, this AATase originated from brewery lager yeast is different from the AATase originated from sake yeast in 332 base pairs and 102 amino acids.

EXAMPLES

The following examples are offered by way of illustration and are not intended to limit the invention any way. In the Examples, all percentages are by weight unless otherwise mentioned.

(1) Preparation of AATase

The enzyme of the present invention can be obtained from the culture of an microorganism which is a member of Saccharomyces and produces an enzyme having the aforementioned properties. The preferred preparation process is as follows:

(1)-(i) Assay of AATase activity

A 1 ml of a solution containing a buffer for AATase reaction (25 mM imidazole hydrochloride buffer (pH 7.5), 1 mM acetyl-CoA, 0.1% Triton X-100, 0.5% isoamyl alcohol, 1 mM dithiothreitol, 0.1M sodium chloride, 20% glycerol; or 10 mM phosphate buffer (pH 7.5), 1 mM acetyl-CoA, 0.1% Triton X-100, 0.5% isoamyl alcohol, 1 mM dithiothreitol, 0.1M sodium chloride, 20% glycerol) and the enzyme of the present invention was encapsulated into a 20 ml vial and reacted at 25° C. for 1 hour. After incubation, the vial was opened and the reaction was stopped by adding 0.6 g of sodium chloride. n-Butanol was added as an internal standard to the reaction mixture up to 50 ppm. The vial was capped with a teflon stopper. Then, the isoamyl acetate generated was determined with the head space gas chromatography (Shimadzu GC-9A, HSS-2A) under the following condition:

Column: glass column 2.1 m×3 mm
Stationary phase: 10% Polyethylene Glycol 1540 Diasolid L (60/80 mesh)
Column temperature: 75° C.
Injection temperature: 150° C.
Carrier gas: nitrogen
Flow rate: 50 ml/min
Sample volume: 0.8 ml.

(1)-(ii) Preparation of crude enzyme

Yeast cells of KYOKAI No. 7 were inoculated in 500 ml of a YPD culture (1% yeast extract, 2% bactopeptone, 2% glucose) and cultured at 15° C. for 3 days. A 25 ml of the culture solution was inoculated into 1000 ml of a YPD culture medium in 20 set of Erlenmeyer flasks having a 200 ml volume and cultured at 30° C. for 12 hours. Cells were then collected by centrifugation (3,000 rpm, 10 min) and suspended into a buffer (50 mM Tris hydrochloride buffer (pH 7.5), 0.1M sodium sulfite, 0.8 M potassium chloride) having a volume 10 times that of the cells. After this, "ZYMOLYASE 100T" (yeast cell cleaving enzyme commercially available from SEIKAGAKU KOGYO K.K.; Japanese Patent No. 702095, U.S. Pat. No. 3,917,510) was added in an amount of 1/1,000 to the weight of the cells. The mixture was incubated with shaking at 30° C. for 1 hour. Then, the resulting protoplast was collected by centrifugation at 3,000 rpm for 5 minutes, suspended in 400 ml of a buffer for the disruption of cells (25 mM imidazole hydrochloride buffer (pH 7.5), 0.6M potassium chloride, 1 mM sodium ethylenediaminetetraacetate (EDTA)) and disrupted with a microbe cell disrupting apparatus "POLYTRON PT10" (KINEMATICA Co.). The cell debris were removed by centrifugation at 45,000 rpm to give a crude enzyme solution.

(1)-(iii) Preparation of microsome fraction

After the crude enzyme solution obtained in (1)-(ii) was centrifuged at 100,000×G for 2 hours, and the resulting precipitate ("microsomal fraction") was suspended in 40 ml of a buffer (25 mM imidazole hydrochloride buffer (pH 7.5), 1 mM dithiothreitol). When the suspension was not immediately used, it was stored at −20° C.

(1)-(iv) Preparation of solubilized enzyme

After the microsomal fraction obtained in (1)-(iii) was placed in a Erlenmeyer flask, Triton X-100 was added in an amount of 1/100 of the volume. The mixture was gently agitated with a magnetic stirrer at 4° C. for 60 minutes so that the mixture was not foamed. The mixture was then centrifuged at 100,000×G for 2 hours. The supernatant was then dialyzed overnight against the buffer A (25 mM imidazole hydrochloride buffer (pH 7.2), 0.1% Triton X-100, 0.5% isoamyl alcohol, 1 mM dithiothreitol, 20% glycerol).

(1)-(v) Purification of enzyme

By repeating the procedures (1)-(ii) and (1)-(iii) twenty times, microsomal fraction was obtained and stored at −20° C. Then by subjecting the procedure (1)-(iv) to the microsomal fraction, the solubilized enzyme fraction for further purification was obtained. The solubilized enzyme fraction was first applied to a POLYBUFFER EXCHANGER 94 column (Pharmacia) (adsorption: buffer A; elution: buffer A+ a gradient of 0.0 to 0.6M sodium chloride).

The active fraction was collected and repeatedly applied to the POLYBUFFER EXCHANGER 94 column.

The active fraction was further purified in the manner as shown in Table 1. That is, the active fraction was purified by (1) ion-exchange column chromatography with DEAE Toyopearl 55 (TOSOH, adsorption: buffer A; elution: buffer A+ a gradient of 0.0 to 0.2M sodium chloride);

(2) gel filtration chromatography with Toyopearl HW60 (TOSOH) using buffer B (10 mM phosphate buffer (pH 7.5), 0.1% Triton X-100, 0.5% isoamyl alcohol, 1 mM dithiothreitol, 0.1M sodium chloride, 20% glycerol);

(3) hydroxyapatite column chromatography (Wako Pure Chemical Industries, Ltd., adsorption: buffer B; elution: buffer B+ a gradient of 10 to 50 mM phosphate buffer (pH 7.5); or (4) octyl sepharose column chromatography (Pharmacia, adsorption: 50 mM imidazole hydrochloride (pH 7.5), 0.5% isoamyl alcohol, 1 mM dithiothreitol, 0.1M sodium chloride, 20% glycerol; elution: 50 mM imidazole hydrochloride (pH 7.5), 0.1% Triton X-100, 0.5% isoamyl alcohol, 1 mM dithiothreitol, 0.1M sodium chloride, 20% glycerol).

As shown in Table 1, AATase was purified approximately 2,000 times on the basis of the specific activity. However, a small amount of other proteins was still observed in SDS-PAGE with silver stain, thus indicating insufficient purification.

Figure 8:
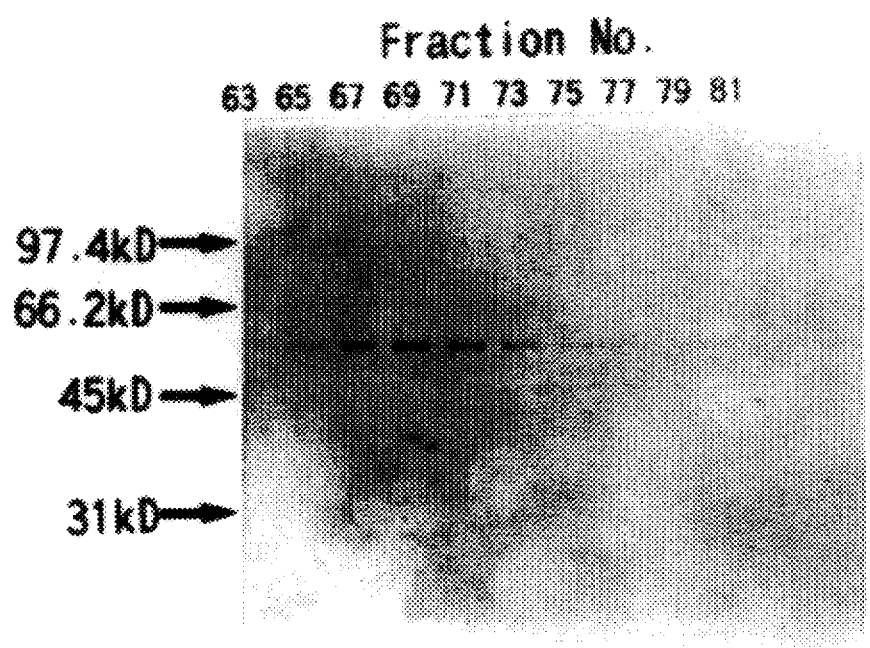
FIG. 8 shows an SDS-polyacrylamide electrophoresis of the AATase active fraction eluted by the affinity chromatography according to the present invention.
Figure 9:
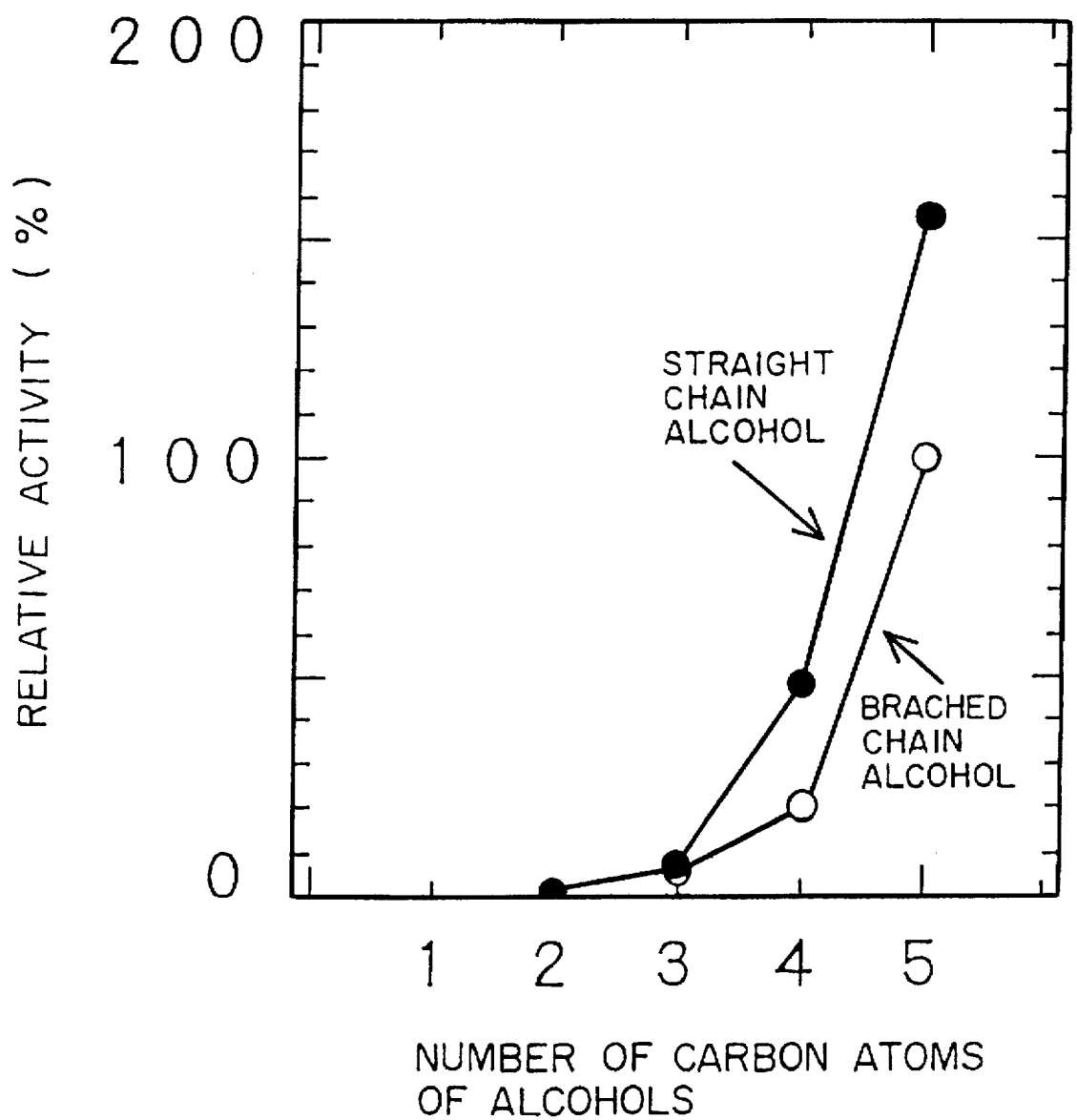
FIG. 9 shows the substrate specificity of the AATase according to the present invention to a variety of alcohols.
Figure 10:
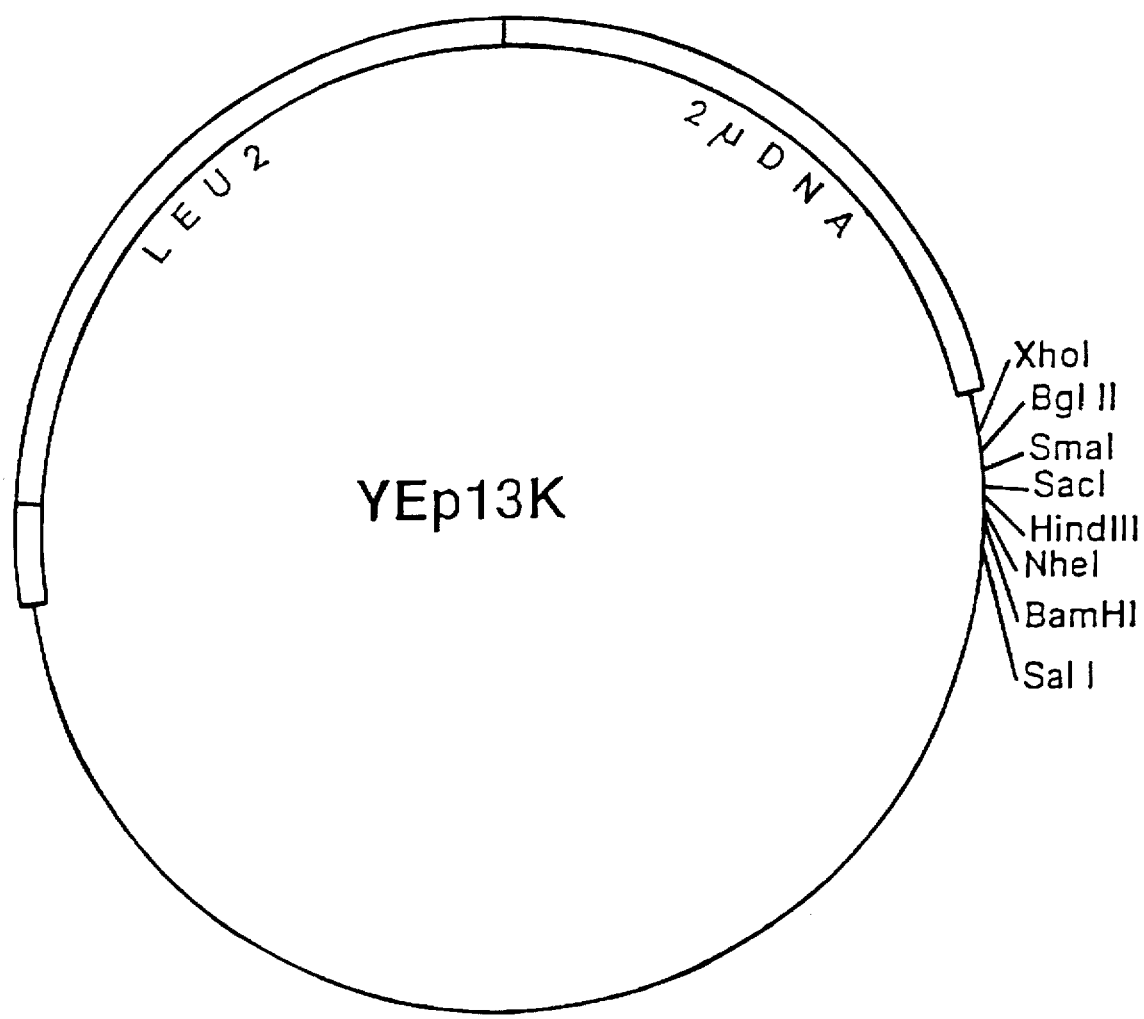
FIG. 10 shows a restriction map of the expression vector YEp13K for yeast.

Thus, the present inventors have carried out affinity chromatography based on the specific affinity between 1-hexanol and AATase. Hexanol Sepharose 4B column was prepared with 6-amino-1-hexanol (Wako Pure Chemical Industries, Ltd.) and CNBr activated Sepharose 4B (Pharmacia) as a support according to the protocol by Pharmacia. Affinity chromatography was conducted with the column (adsorption: 5 mM phosphate buffer (pH 7.2), 0.1% Triton X-100, 20% glycerol, 1 mM dithiothreitol; elution: sodium chloride with a gradient from 0.0 to 0.2M). The active fraction thus obtained as shown in FIG. 9 was subjected to SDS-PAGE and stained with silver. The AATase was successfully purified to homogeneity since the active fraction was n enzyme which afforded a single band as shown in FIG. 8.

TABLE 1

Purification of AATase

| | Volume (ml) | Activity (ppm/ml) | Total activity (ppm) |
|---|---|---|---|
| Solubilized enzyme | 505 | 119 | 60100 |
| PBE 94 1st. | 395 | 77 | 30400 |
| PBE 94 2nd | 86 | 304 | 26100 |
| DEAE Toyopearl | 24 | 580 | 13900 |
| Toyopearl HW60 | 24 | 708 | 17000 |
| Hydroxy apatite | 7.6 | 1020 | 7750 |
| Octyl sepharose | 1.0 | 2390 | 2390 |

| | Protein (mg/ml) | Specific activity (ppm/mg protein) | Yield (%) | Rate of Purification |
|---|---|---|---|---|
| Solubilized enzyme | 5.43 | 22 | 100 | 1 |
| PBE 94 1st. | 0.515 | 150 | 51 | 7 |
| PBE 94 2nd. | 1.086 | 280 | 43 | 13 |
| DEAE Toyopearl | 0.96 | 604 | 23 | 27 |
| Toyopearl HW60 | 0.262 | 2700 | 28 | 123 |
| Hydroxy apatite | 0.119 | 8570 | 13 | 266 |
| Octyl sepharose | 0.056 | 42700 | 4 | 1940 |

(2) Properties of AATase (2)-(i) Substrate specificity

According to studies of substrate specificity of AATase to various kinds of alcohol by using the aforementioned analytical apparatuses and methods, AATase acts on a variety of alcohol having 1–5 carbon atoms. AATase acts more efficiently on alcohols having higher number of carbon atoms. In addition, AATase acts more efficiently on straight chain alcohols rather than branched chain alcohols (FIG. 9).

(2)-(ii) Optimum pH and pH stability

In order to examine the effect of pH on the stability of the enzyme, the enzyme was maintained at respective pH of from pH 5 to 9 (pH 5–6: 50 mM citrate-phosphate buffer; pH 6–8: 50 mM phosphate buffer; pH 8–9: 50 mM Tris-phosphate buffer) under the condition of 4° C. for 22 hours. The enzyme activity was assayed at pH 7.5 with 0.2M disodium phosphate according to the method (1)-(i).

In order to evaluate the effect of pH on the activity of the enzyme, the enzyme activities were assayed at respective pH of from 5 to 9 (pH 5–6: 50 mM citrate-phosphate buffer; pH 6–8: 50 mM phosphate buffer; pH 8–9: 50 mM Tris-phosphate buffer) according to the method (1)-(i).

The enzyme of the present invention was stable within the pH range from 7.5 to 8.5. The optimum pH was 8.0.

(2)-(iii) Optimum temperature and thermal stability

In order to examine the effect of temperature on the activity of the enzyme, the enzyme activities were assayed at various temperatures according to the method of (1)-(i).

In addition, after the enzyme incubated at each temperature for 30 minutes, the enzyme activities were assayed according to the method of (1)-(i).

The optimum temperature was 25° C. The enzyme was stable at 4° C., but it was very unstable at a temperature of higher than 4° C.

(2)-(iv) Inhibition

For the examination of effects of various inhibitors on the enzyme activity, enzyme assay was carried out in a reaction buffer described in (1)-(i) containing inhibitors (1 mM) shown in Table 2 according to the method of (1)-(i). The results are shown in Table 2. The enzyme according to the present invention is believed to be an SH enzyme, because it was inhibited strongly by p-chloromercuribenzoic acid (PCMB) and dithiobis(2-nitrobenzoic acid) (DTNB).

TABLE 2

| Inhibitor (1 mM) | Relative activity (%) | Inhibitor (1 mM) | Relative activity (%) |
|---|---|---|---|
| None | 100 | $ZnCl_2$ | 12.7 |
| KCl | 98.6 | $MnCl_2$ | 53.3 |
| $MgCl_2$ | 86.2 | $HgCl_2$ | 0 |
| $CaCl_2$ | 87.7 | $SnCl_2$ | 52.0 |
| $BaCl_2$ | 73.7 | TNBS* | 16.8 |
| $FeCl_3$ | 54.5 | PCMB* | 0 |
| $CoCl_2$ | 37.6 | DTNB* | 0 |
| $CdCl_2$ | 3.1 | PMSF* | 70.2 |
| $NiCl_3$ | 22.3 | 1,10-phenanthroline | 87.9 |
| $CuSO_4$ | 0 | | |

*1 mM TNBS: Trinitrobenzenesulfonic acid,
0.1 mM PCMB: p-Chloromercuribenzoic acid
0.1 mM DTNB: Dithiobis(2-nitrobenzoic acid)
1 mM PMSF: Phenylmethanesulfonyl fluoride.

(2)-(v) Effects of fatty acids on enzyme activity

Various fatty acids were added in an amount of 2 mM to the reaction buffer of (1)-(i) to examine the effect of the fatty acids on the enzyme activity. The activity was assayed according to the method (1)-(i). The results are shown in Table 3.

TABLE 3

Influence of fatty acids on the enzyme activity

| Fatty acid (2 mM) | | Relative activity (%) |
|---|---|---|
| None | | 100 |
| Myristic acid | $C_{14}H_{28}O_2$ | 60.5 |
| Palmitic acid | $C_{16}H_{32}O_2$ | 88.1 |
| Palmitoleic acid | $C_{16}H_{30}O_2$ | 16.7 |
| Stearic acid | $C_{18}H_{36}O_2$ | 80.5 |
| Oleic acid | $C_{18}H_{34}O_2$ | 59.6 |
| Linoleic acid | $C_{18}H_{32}O_2$ | 4.3 |
| Linolenic acid | $C_{18}H_{30}O_2$ | 32.0 |

(3) Sequencing partial amino acid sequence

Partial amino acid sequence was determined according to the method described by Iwamatsu (SEIKAGAKU, 63, 139 (1991)) using a polyvinylidene difluoride (PVDF) membrane. The AATase prepared in (1)-(v) was dialyzed against 3 liter of 10 mM formic acid for 1 hour and then lyophilized. The lyophilized enzyme was suspended in a buffer for electrophoresis (10% glycerol, 2.5% SDS, 2% 2-mercaptoethanol, 62 mM Tris hydrochloride buffer (pH 6.8)) and subjected to SDS-PAGE. Then, the enzyme was electroblotted onto a PVDF membrane of 10 cm×7 cm ("ProBlot", Applied Biosystems) using ZARTBLOT IIs model (ZARTRIUS Co.). The electroblotting was carried out at 160 mA for 1 hour according to "Pretreatment method of a sample in PROTEIN SEQUENCER (1)" edited by SHIMAZDU SEISAKUSHO.

PVDF-immobilized enzyme was then cut off and dipped into about 300 μl of a buffer for reduction (6M guanidine hydrochloride –0.5M Tris hydrochloride buffer (pH 3.5), 0.3% EDTA, 2% acetonitrile) with 1 mg of dithiothreitol (DTT) and reduced under argon at 60° C. for about 1 hour. A solution of 2.4 mg of monoiodoacetic acid in 10 μl of 0.5 N sodium hydroxide was added. The mixture was then stirred in darkness for 20 minutes. After the PVDF membrane was taken out and washed sufficiently with 2% acetonitrile, the membrane was further stirred in 0.1% SDS for 5 minutes. The PVDF membrane was next rinsed lightly with water, dipped into 0.5% polyvinylpyrrolidone –40 –100 mM acetic acid and left standing for 30 minutes. The PVDF membrane was washed thoroughly with water and cut into square chips having a side of about 1 mm. The chips were dipped into a digestion buffer (8% acetonitrile, 90 mM Tris hydrochloride buffer (pH 9.0)) and digested at room temperature for 15 hours after 1 pmol of ACROMO-BACTER PROTEASE I (Wako Pure Chemical Industries, Ltd.) was added. The digested products was separated by reverse phase high performance liquid chromatography (model L6200, HITACHI) with a C8 column (NIPPON MILIPORE, LTD; μ-Bondasphere 5C8, 300A, 2.1×150 mm) to give a dozen or so peptide fragments. The elution of the peptide was carried out using the solvent A (0.05% trifluoroacetic acid) with a linear gradient from 2 to 50% of the solvent B (2-propanol/acetonitrile (7:3) containing 0.02% trifluoroacetic acid) at a flow rate of 0.25 ml/min. The amino acid sequencing of the peptide fragments thus was conducted by the automatic Edman degradation method with a vapor phase protein sequencer model 470 (Applied Biosystems) according to manufacturer's instructions.

As a result, the following amino acid sequences were determined:

| peak 1 | Lys Trp Lys |
|---|---|
| peak 2 | (SEQ ID NO: 1) Lys Tyr Val Asn Ile Asp |
| peak 3 | (SEQ ID NO: 2) Lys Asn Gln Ala Pro Val Gln Gln Glu Cys Leu |
| peak 4 | (SEQ ID NO: 3) Lys Gly Met Asn Ile Val Val Ala Ser |
| peak 5 | (SEQ ID NO: 4) Lys Tyr Glu Glu Asp Tyr Gln Leu Leu Arg Lys |
| peak 6 | (SEQ ID NO: 5) Lys Gln Ile Leu Glu Glu Phe Lys |
| Peak 7 | (SEQ ID NO: 6) Lys Leu Asp Tyr Ile Phe Lys |
| Peak 8 | (SEQ ID NO: 7) Lys Val Met Cys Asp Arg Ala Ile Gly Lys |
| Peak 9 | (SEQ ID NO: 8) Lys Leu Ser Gly Val Val Leu Asn Glu Gln Pro Glu Tyr |
| peak 10 | (SEQ ID NO: 9) Lys Asn Val Val Gly Ser Gln Glu Ser Leu Glu Glu Leu Cys Ser Ile Tyr Lys |

(4) Cloning of DNA encoding AATase from sake yeast
(i) Preparation of sake yeast library Yeast cells of KYOKAI No. 7 were grown in 1 liter of a YPD medium up to O.D.600=10, collected and washed with sterilized water. The cells were suspended in SCE solution (1M sorbitol, 0.125M EDTA, 0.1M trisodium citrate (pH 7), 0.75% 2-mercaptoethanol, 0.01% "ZYMOLYACE 100T" (SEIKAGAKU KOGYO K.K.) in a ratio of 2 ml of SCE solution per 1 g of the cells, incubated at 37° C. for about 2 hours and protoplastized completely. The resulting protoplast was suspended in Lysis Buffer (0.5M Tris hydrochloride buffer (pH 9), 0.2M EDTA, 3% sodium dodecyl sulfate (SDS)) in an ratio of 3.5 ml of the buffer per 1 g of the cells. The mixture was then stirred gently at 65° C. for 15 minutes to lyse the cells completely. After the lysis, the mixture was cooled to room temperature, a 10 ml of the mixture was cautiously placed on each of 23.5 ml of 10%–40% sucrose density gradient solution (0.8M sodium chloride, 0.02M Tris hydrochloride buffer (pH 8), 0.01M EDTA, 10%–40% sucrose) which had been previously prepared in HITACHI ultracentrifugation tubes 40PA. It was centrifuged with a HITACHI ULTRACENTRIFUGE SCP85H at 4° C. and 26,000 rpm for 3 hours. After the centrifugation, the resulted solution was recovered with a graduated pippete (komagome) in an amount of about 5 ml from the bottom of the tube. The DNA sample thus recovered was dialyzed overnight against 1 liter of a TE solution.

The chromosomal DNA thus obtained was partially digested with Sau3AI according to the method by Frischauf et al. (Methods in Enzymology, 152, 183, Academic Press, 1987), placed again on 10%–40% sucrose density gradient solution and centrifuged at 20° C. and 25,000 rpm for 22 hours. After centrifugation, the ultracentrifugation tube was pierced at the bottom with a needle, and 0.5 ml of the density gradient solution was fractionated in every sampling tube. A portion of each fraction was subjected to agarose gel electrophoresis to confirm the molecular weight of the chromosomal DNA. Then, the 15–20 kb DNA was collected and recovered by ethanol precipitation.

The digested chromosomal DNA (1 μg) and the λ-EMBL3 vector (1 μg) of a λ-EMBL3/BamH1 vector kit (manufactured by STRATAGENE, purchased from FUNAKOSHI) were ligated at 16° C. overnight. The ligation product was packaged using a GIGAPACK GOLD (manufactured by STRATAGENE, purchased from FUNAKOSHI). The ligation and packaging were conducted according to manufacturer's instructions.

The host strain P2392 of the μ-EMBL3 vector kit was infected with a 50 μl of the packaged solution. One inoculation loop amount of P2392 was cultured in 5 ml of a TB culture medium (1% bactotriptone (DIFCO), 0.5% sodium chloride, 0.2% maltose, pH 7.4) at 37° C. overnight. Then, 1 ml of the culture was inoculated into 50 ml of a TB culture medium and cells were grown up to O.D. 600=0.5. After the culture fluid was cooled on an ice bath, the cells were collected by centrifugation and suspended in 15 ml of an ice-cooled 10 mM magnesium sulfate solution. To 1 ml of the cells were added 0.95 ml of an SM solution (0.1M sodium chloride, 10 mM magnesium sulfate, 50 mM Tris hydrochloride buffer (pH 7.5), 0.01% gelatin) and 50 μl of the packaging solution. The mixture was slightly stirred and kept at a temperature of 37° C. for 15 minutes. A 200 μl portion of the mixture was added into 7 ml of a BBL soft agar culture medium (1% Tripticase peptone (BBL), 0.5% sodium chloride, 0.5% agarose (Sigma)) which had been maintained at a temperature of 47° C. The mixture was slightly mixed and overlaid for spreading on a BBL agar plate (1% Tripticase peptone, 0.5% sodium chloride, 1.5% Bactoagar (DIFCO)) having a diameter of 15 cm.

The overlaid plate was incubated at a temperature of 37° C. for 8 hours. A pharge library which contains approximately 30,000 clones having yeast chromosmal DNA fragments, on 10 overlaid agar plates were thus obtained.

The library was transferred to a nylon membrane for cloning. A hybridization transfer membrane (NEN) having a diameter of 15 cm was contacted with the overlaid agar plate for about 2 minutes to prepare two sets of the membranes on which the phages were transferred and 20 sheets in total. The membranes were placed with the surface which had been contacted with the agar plate up on a filter paper impregnated with an alkali denaturating solution (1.5M sodium chloride, 0.5 N sodium hydroxide) and left standing for about 5 minutes. The membranes were then displaced on a filter paper impregnated with a neutralizing solution (3M sodium acetate (pH 5.8)), left standing for about 5 minutes, then dried at room temperature and further dried in vacuum at 80° C. for 1 hour. The agar plate from which the library had been transferred were stored at 4° C.

(ii) Synthesis and Labelling of probes

The following synthetic probes were prepared using a DNA synthesizer "Model 380B" (manufactured by APPLIED BIOSYSTEMS) on the basis of the partial amino acid sequence of Peak 5 and Peak 2 obtained in (3):

Probe 5 (amino acid residues 1–6 of SEQ ID NO:4)

Lys Tyr Glu Glu Asp Tyr (Peak 5), SEQ ID NO:10  5'-AAA TAT GAA GAT TAT CA-3'
                              G    C    G    C    C -continued Probe 2 (amino acid residues 1–4 of SEQ ID NO:1)

Lys Tyr Val Asn Ile (SEQ ID NO:11) 5'-AAA TAT GTA AA T ATT GA-3'
```
              G   C   G   C   C
                          C       A
                          T
```

All of the synthesis reagents such as phosphoamidite were purchased from APPLIED BIOSYSTEMS and were used according to manufacturer's instructions.

The synthetic DNA thus obtained was treated with 3 ml of an 28% aqueous ammonia at 60° C. for 4 hours and then purified with an Oligonucleotide Purification Cartriges manufactured by APPLIED BIOSYSTEMS.

The two synthetic probes were individually labelled with [γ-$^{32}$P]ATP (ca. 6000 Ci/mM). Each probe DNA (ca. 250 ng) was subjected to reaction in 200 µl of a reaction solution containing 10 units of T4 polynucleotide kinase, 500 µCi of [γ-$^{32}$P]ATP and a phosphate buffer (0.1 mM spermidine, 0.1 mM EDTA, 10 mM magnesium chloride, 5 mM DTT, 50 mM Tris hydrochloride (pH 7.6)) at 37° C. for 1 hour, and kept at a temperature of 70° C. for 10 minutes. Unincorporated [γ-$^{32}$P]ATP was removed by the purification with a DE52 manufactured by WATTMAN.

(iii) Cloning by plaque hybridization

The cloning by plaque hybridization was carried out by first, second and third screenings as follows:

In the first screening, 20 sheets of the membrane on which the yeast library prepared in (4)-(i) had been transferred were dipped into 200 ml of a hybridization solution (6× SSPE (1.08M sodium chloride, 0.06M sodium phosphate, 6 mM EDTA, pH 7.4), 5× a Denhardt's solution (0.1% polyvinylpyrrolidone, 0.1% Ficoll, 0.1% bovine serum albumin), 0.5% SDS, 10 µg/ml single strand salmon sperm DNA) and incubated for prehybridization at 60° C. for 3 hours.

The [γ-$^{32}$P]ATP labelled probe 5 prepared in (4)-(ii) was kept at 95° C. for 5 minutes and cooled with ice-water. The twenty sheets of the prehybrized membrane were dipped into a mixed solution of the denatured probe 5 and 400 ml of a hybridization solution and incubated gently at 30° C. overnight to hybridize the membrane with the labelled probe 5.

The hybridization solution was discarded. In order to remove the excessive probe 5 from the membrane, the membrane was shaken gently in 400 ml of 2× SSC (0.3M sodium chloride, 0.03M sodium citrate) at 30° C. for 20 minutes. The membrane was then contacted with a X-ray film and exposed at −80° C. overnight. As positive clones 49 plaques which had sensitized both of the two sheets were subjected to the second screening.

In the second screening, these plaques on the original agar plates were picked with an aseptic Pasteur's pipette and suspended into 1 ml of SM. After A 1/100 dilution of the suspension was prepared, 100 µl of the P2392 microbial solution was infected with a 100 µl portion of the dilution in the same manner as in the preparation of the library, mixed with 3 ml of a BBL soft agar medium and overlaid on a BBL agar plates having a diameter of 9 cm. After plaques had appeared, 49 sets of two membrane sheets to one clone were prepared in the same manner as described in (3)-(iii). The same procedure as in the first screening was repeated with the [γ-$^{32}$P]ATP labelled probe 2 which had been prepared in (4)-(ii). Fifteen plaques as the positive clones were subjected to the third screening.

In the third screening, using the [γ-$^{32}$P]ATP labelled probe 5, the same procedure as in the second screening was repeated. Finally, 14 positive clones were obtained.

An overnight culture of E. coli P2392 in TB medium was concentrated four times in TB medium containing 10 mM MgSO$_4$. Then 20 µl of each positive clone which had been prepared in a concentration of 109 to 1010 plaque/ml was infected to 5 ml of this cell suspension. This infected all suspension was kept at 37° C. for 15 minutes, then inoculated into 50 ml of TB medium containing 10 mM MgSO$_4$ and cultured for 6 hours with shaking. Then, CCl$_4$ was added to the cell culture and the culture was incubated with shaking at 37° C. for 30 minutes to lyse P2392 and centrifuged at 10,000 rpm for 10 minutes to recover the supernatant. DNase (TAKARA SHUZO) and RNase (BERINGER-MANNHEIM) were added to the supernatant up to 10 µg/ml, respectively. The mixture was then kept at 37° C. for 30 minutes. After the polyethylene glycol solution (20% Polyethylene Glycol 6000, 2.5M sodium chloride) was added in an amount of 30 ml, the mixture was left standing at 4° C. overnight. Centrifugation was conducted at 10,000 rpm for 10 minutes. After the supernatant was discarded, the precipitate was suspended in 3 ml of SM. EDTA (pH 7.5) and SDS were added to the suspension up to 20 mM and 0.1%, respectively. The mixture was kept then at 55° C. for 4 minutes followed by adding the phenol solution (phenol (25): chloroform (24): isoamyl alcohol (1)). The mixture was slowly stirred for 10 minutes, centrifuged 10,000 rpm for 10 minutes to recover the DNA layer (aqueous layer). After this procedure was repeated again, 0.33 ml of 3M sodium acetate and 7.5 ml of ethanol were added to the aqueous layer, and the mixture was stirred and left standing at −80° C. for 30 minutes. After the mixture was centrifuged at 10,000 rpm for 10 minutes, the precipitate was rinsed with 70% ethanol, then remove 70% ethanol, and the precipitate was dried up and dissolved in 500 µl of TE. Each of the phage DNAs thus obtained was cut with a variety of restriction enzymes and compared with each other by electrophoresis. Although the fourteen positive clones appeared consist of not only those containing the whole of the DNA sequence capable of producing AATase but those having partial deletions, all of the clones were those which cloned the identical site on the yeast chromosome. The restriction map of 6.6 kb XbaI fragment containing the whole length of the DNA sequence among these clones are shown in FIG. 3. The DNA sequencing was carried out according to the dideoxy method with a XbaI fragment which had been subcloned in pUC119 (TAKARA SHUZO). The DNA sequence of the gene encoding AATase is shown in FIGS. 1(a) through 1(f) (SEQ ID NO:14).

(5) Preparation of DNA encoding AATase from brewery lager yeast

Figure 6:
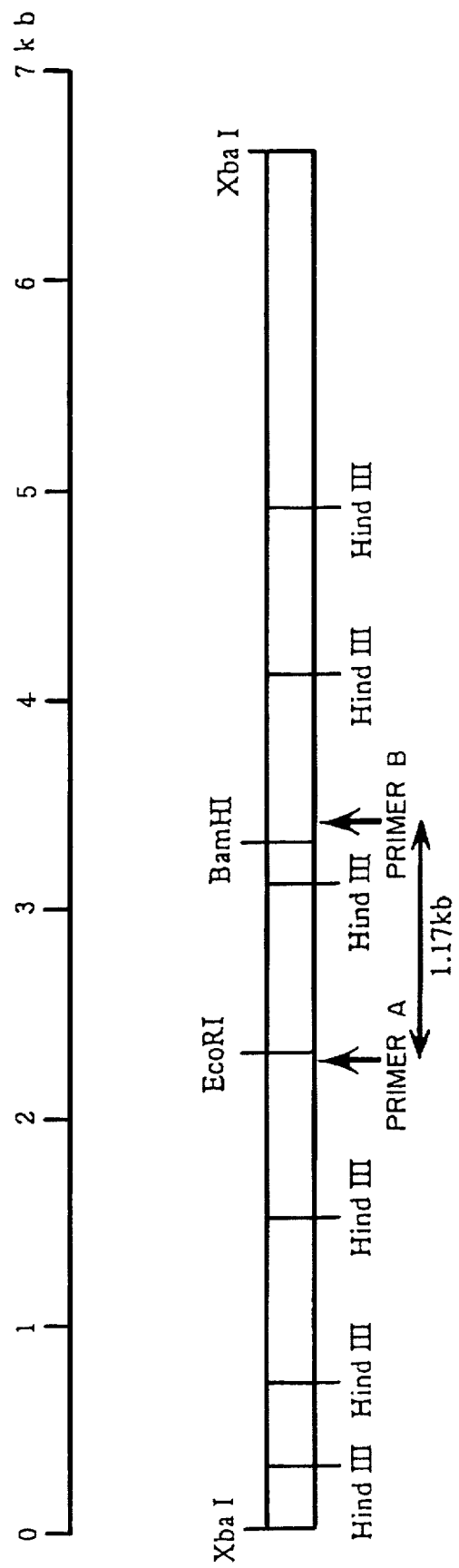
FIG. 6 shows the process for preparing the probe used for obtaining the AATase gene from the wine yeast (SEQ ID NO:12 and 13 correspond to Primers A and B, respectively)

Using the sake yeast AATase gene as a probe, a DNA strands hybridized with the sake yeast (KYOKAI No. 7) AATase gene were cloned from brewery lager yeast. The 1.6 kb HindIII (the range within the arrow) fragment shown in FIG. 3 (50 ng) was reacted with 100 µCi of [α-$^{32}$P]dCTP (ca. 3,000 Ci/mM) using a Multiprime Labelling Kit (AMERSHAM JAPAN K.K.). Cloning by plaque hybridization was performed with this reaction product as a probe and the brewery lager yeast library containing 30,000 phage clones prepared in the same manner as described in (4)-(i). Hybridization temperature was set at 50° C. The membranes were gently incubated at 50° C. in 2× SSC for 30 minutes and in 0.2× SSC (0.03M sodium chloride, 3 mM sodium citrate) for 30 minutes in order to remove the excessive probes. In the first screening, 60 positive clones were obtained. These positive plaques were subjected to the second screening in the same manner as described in (4)-(iii). Hybridization was repeated with the same probe under the same condition as described above to give 30 positive clones. DNA was extracted from these positive clones and subjected to restriction analysis. The results shows that those positive clones are two groups. The restriction maps of the insert DNA of these two groups are quite different, thus it has been suggested these insert DNAs present on different locus of yeast chromosome. FIG. 6 show the restriction maps of the DNA fragment containing AATase 1 and 2. These clones are referred to hereinafter as "brewery yeast AATase 1 gene" and "brewery yeast AATase 2 gene", respectively.

The DNA sequence of the brewery yeast AATase 1 gene and the brewery yeast AATase 2 gene were determined in the same manner as described in (4)-(iii). The DNA sequences of the brewery yeast AATase 1 gene and the brewery yeast AATase 2 gene are shown in FIGS. 2(a)–2(f) and 17(a)–17 (f) SEQ ID NO:16) SEQ ID NO:18), respectively. The AATase 2 gene was a DNA fragment which produces a polypeptide having an AATase activity in either case of the DNA sequence from A to C or the DNA sequence from B to C.

(6) Preparation of a vector containing an AATase gene and cultivation of a yeast transformed by the vector (i) Construction of an expression vector for *Saccharomyces cerevisiae*

Figure 11:
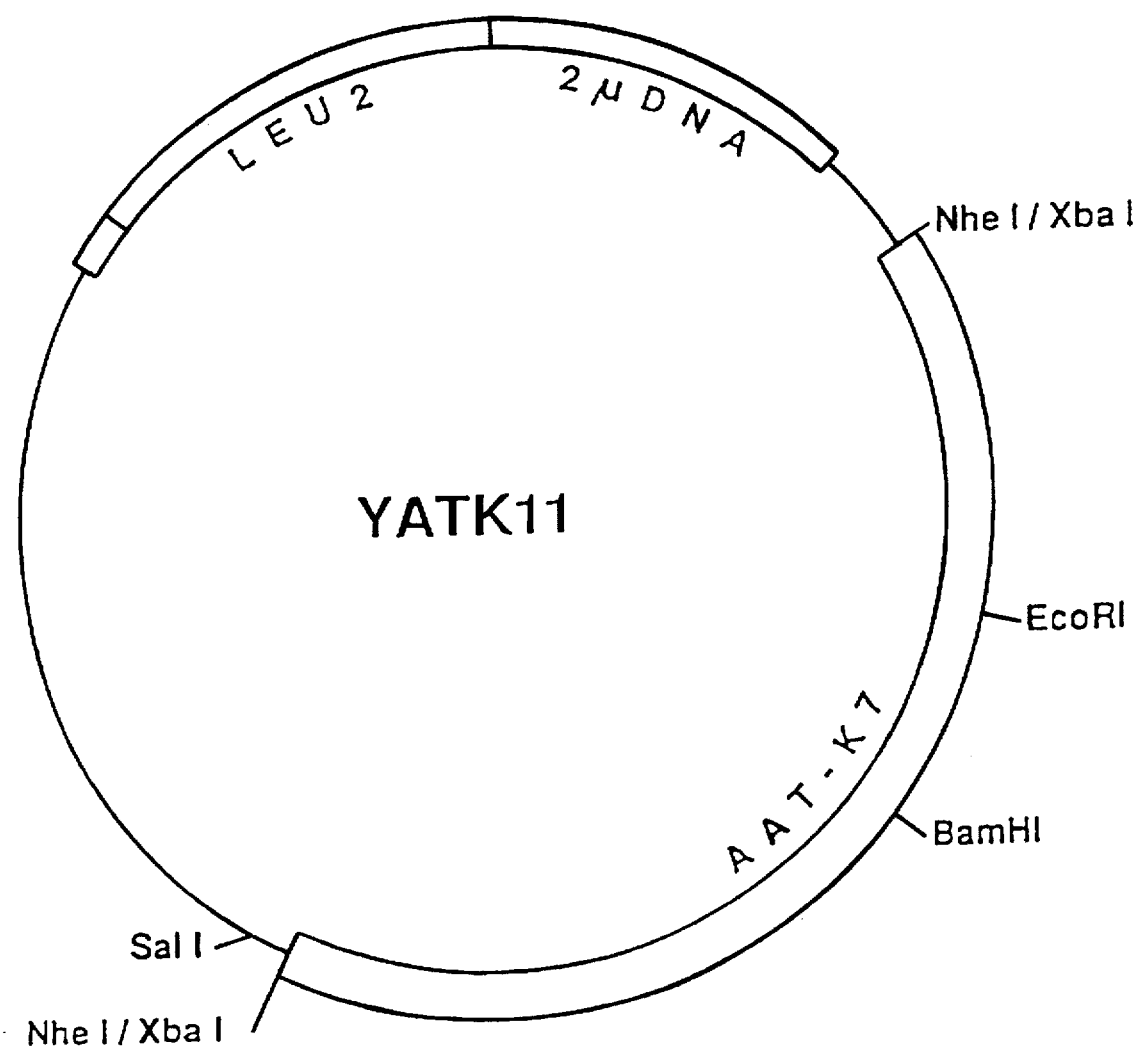
FIG. 11 shows a restriction map of the expression vector YATK11 having the AATase gene originated from a sake yeast according to the present invention.

A 6.6 kb XbaI fragment (AAT-K7) of the sake yeast AATase gene obtained in (4)-(iii) and shown in FIG. 3 was prepared. The fragment was cloned into the NheI site of the yeast vector YEp13K containing the replication origin of the yeast 2 μm DNA and the yeast LEU2 gene as a marker to construct the expression vector YATK11 (FIGS. 11).

Figure 12:
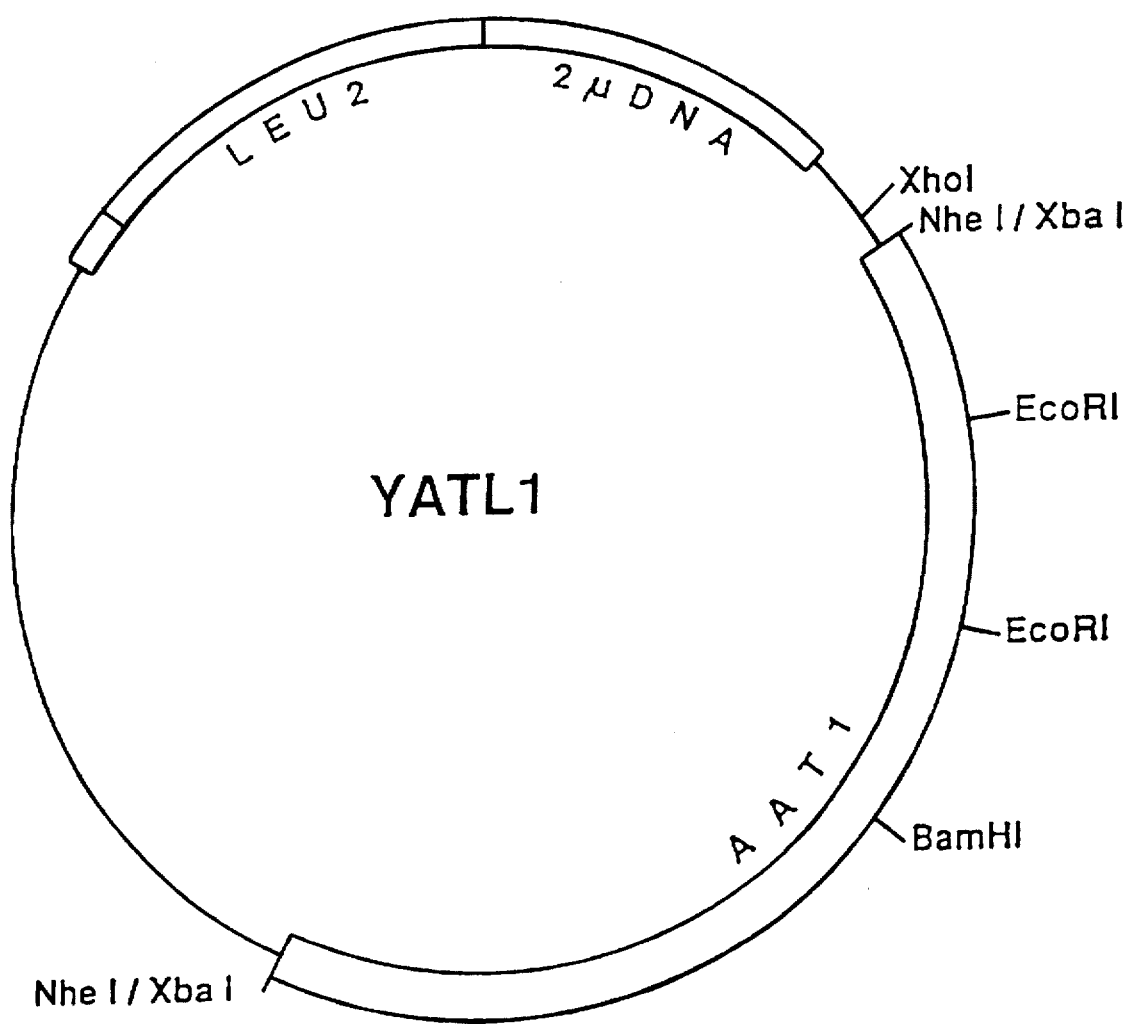
FIG. 12 shows a restriction map of the expression vector YATL1 having the AATase 1 gene originated from a brewery lager yeast according to the present invention.

In the same manner, a 6.6 kb XbaI fragment (AAT-1) of the brewery yeast AATase gene 1 obtained in (5) and shown in FIG. 4 was cloned into the NheI site of YEp13K to construct the expression vector YATL1 (FIGS. 12).

Figure 13:
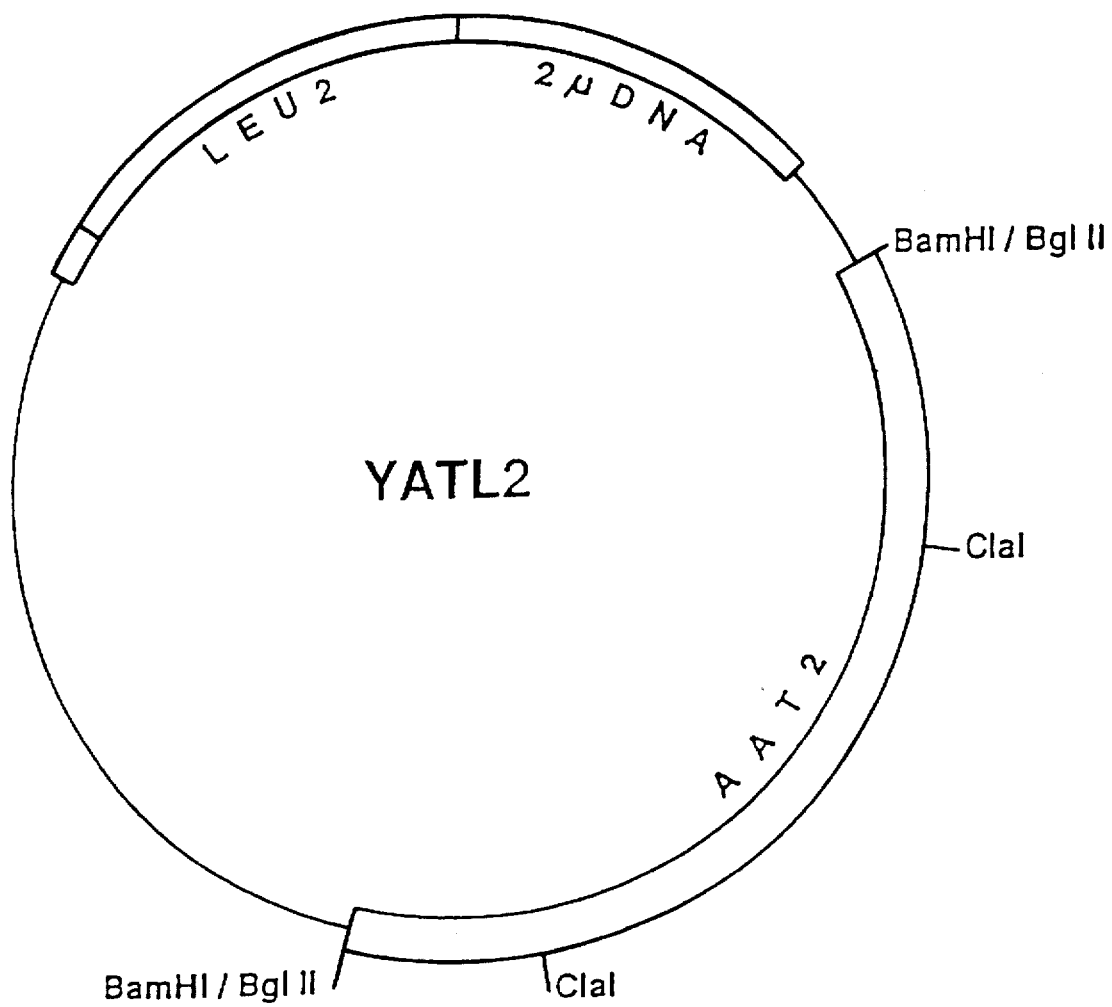
FIG. 13 shows a restriction map of the expression vector YATL2 having the AATase 2 gene originated from a brewery lager yeast according to the present invention.

In addition, a 5.6 kb BglII fragment (AAT-2) of the brewery yeast AATase gene 2 shown in FIG. 4 was cloned into the BamHI site of YEp13K to construct the expression vector YATL2 (FIGS. 13).

(ii) Construction of an expression vector for sake yeast KYOKAI No. 9

Figure 14:
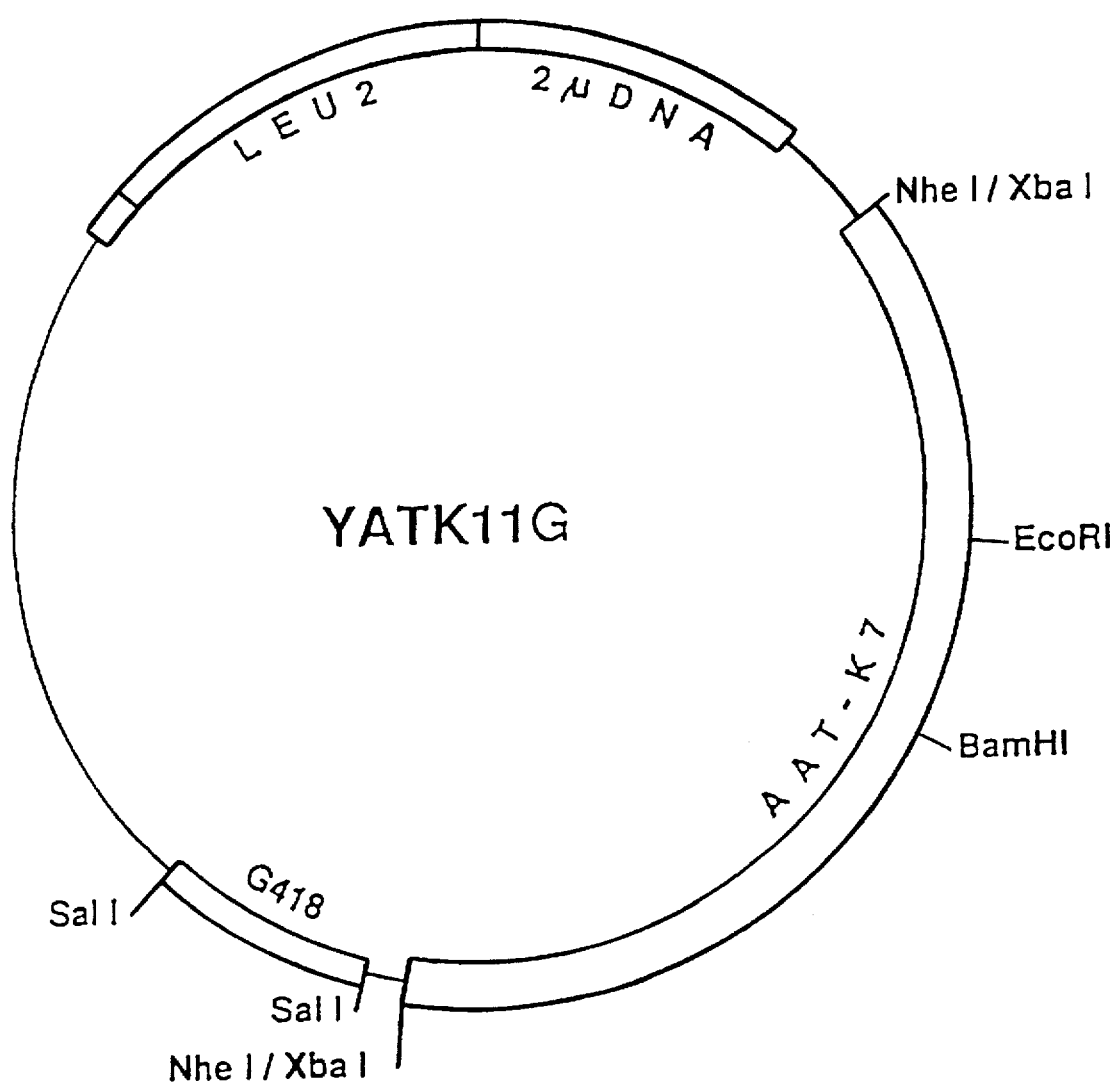
FIG. 14 shows a restriction map of the sake-yeast expression vector YATK11G having the AATase gene originated from a sake yeast according to the present invention.

Plasmid pUC4k (Pharmacia) containing a G418 resistant gene was cut with SalI. Then, the resulting fragment containing the G418 resistant gene was cloned into the SalI site of the YATK11 to construct a vector YATK11G for transfecting the AATase gene into sake yeast (FIGS. 14).

(iii) Construction of an expression vector for brewery lager yeast (iii-a) Preparation of G418 resistant marker The 2.9 kb HindIII fragment containing PGK gene (Japanese Patent Laid-Open Publication No. 26548/1990) was cloned into pUC18 (TAKARA SHUZO). Plasmid pUCPGK21 containing a PGK promoter and a terminator was shown in FIGS. 16.

Figure 16:
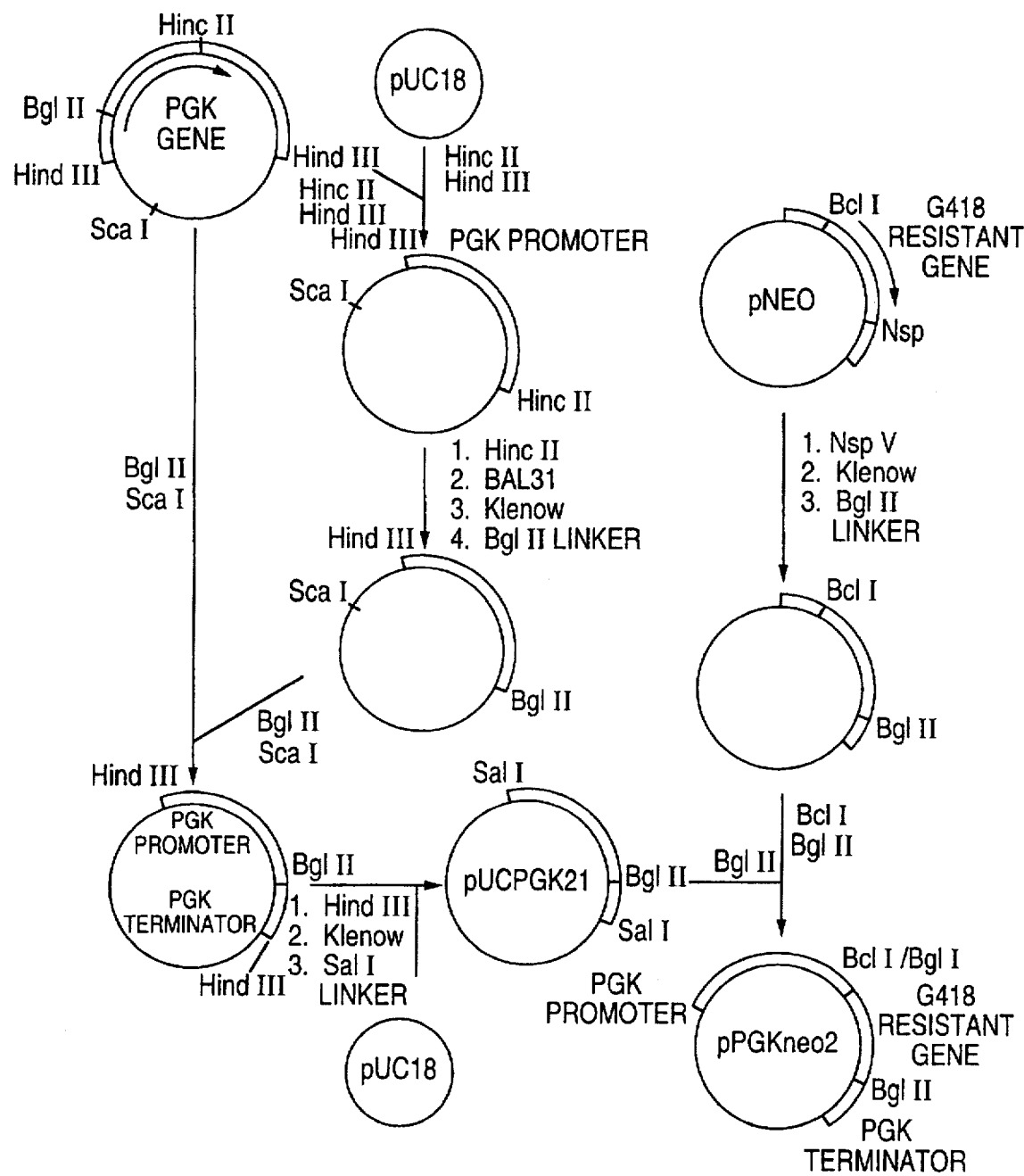
FIG. 16 shows a part of the brewery lager yeast expression vector construction.

G418 resistant gene was cloned from the plasmid pNEO (Pharmacia) into the pUCPGK21 by the process described in FIGS. 16 to construct pPGKneo2.

Figure 15:
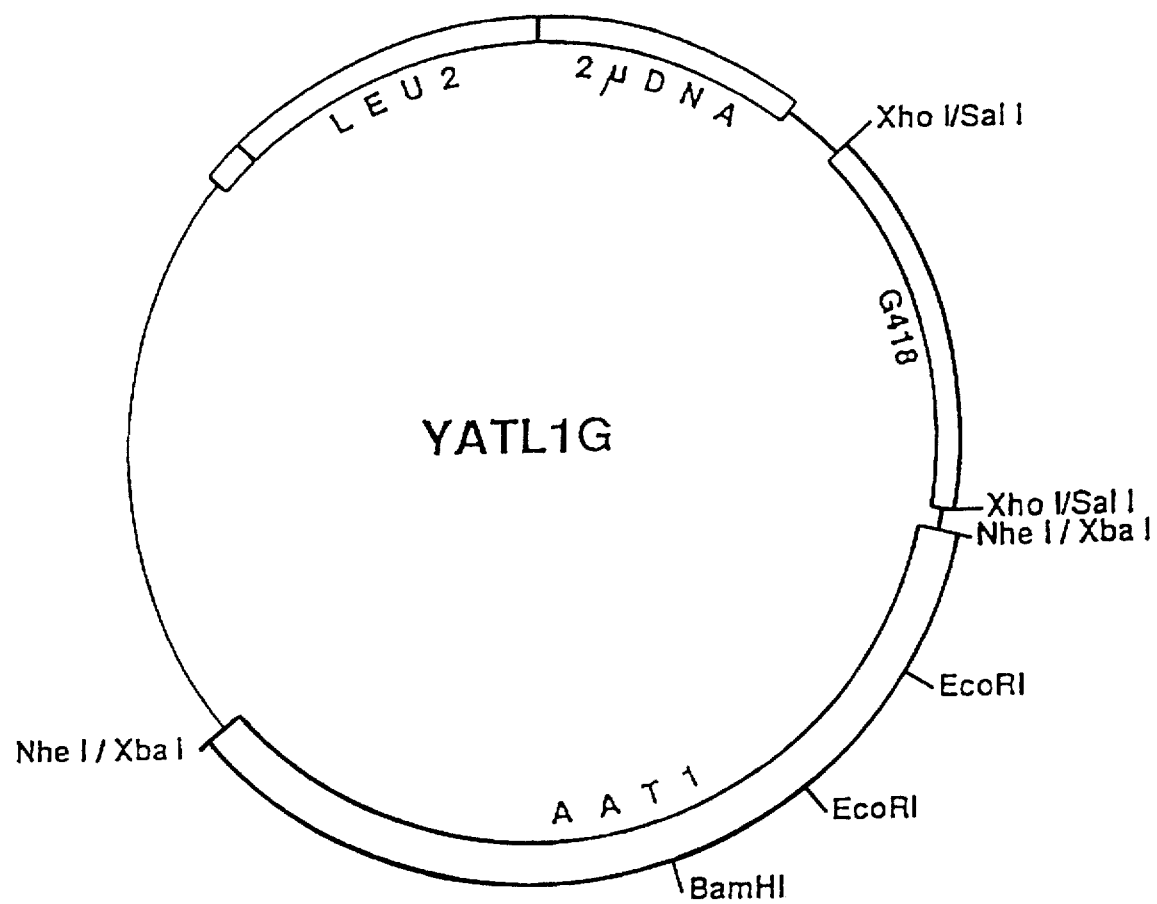
FIG. 15 shows a restriction map of the brewery lager yeast vector YATL1G having the AATase 1 gene originated from a brewery lager yeast according to the present invention.

(iii-b) Construction of expression vectors pPGKNEO2 was digested with SalI to generate the ca. 2.8 kb fragment containing the PGK promoter, the G418 resistant gene and the PGK terminator. This fragment was then cloned into the XhoI site of YATL1 to construct YATL1G (FIGS. 15).

(7) Transformation of yeasts with AATase gene

In order to confirm that the cloned AATase genes in (4)-(iii) and (5) Produces AATase, yeast cells were transformed with these vectors prepared in (6), and AATase activity of the transformants were measured.

The transfection of the plasmid into *Saccharomyces cereviciae* TD4 (a, his, leu, ura, trp) was carried out according to the lithium acetate method (J. Bacteriol., 153, 163 (1983)) to give YATK11/TD4, YATL1/TD4 and YATL2/TD4 (SKB105 strain).

The transformant of SAKE YEAST KYOKAI NO. 9 (SKB106 strain) was obtained according to the following procedure. The strain, in to which the plasmid had been transfected by the lithium acetate method, was spread onto YPD agar plates containing G418 (300 μl/ml). The plates were incubated at 30° C. for 3 days. Colonies grown up were inoculated again in a YPD agar medium containing G418 (500 g/ml) and cultured at 30° C. for 2 days to give the transformants.

YATL1G was transfected into the strain 2155 of the brewery lager yeast Alfred Jorgensen Laboratory (Denmark) (AJL2155 strain) in the following procedure. The yeast was cultured with shaking in 100 ml of a YPD medium at 30° C. until O.D.600=16. Cells were collected, rinsed once with sterilized water, then rinsed once with 135 mM Tris buffer (pH 8.0) and suspended in the same buffer so that the suspension had a microbial concentration of $2 \times 10^9$ cells/ml. To 300 μl of the suspension were added 10 μg of YATL1G, 20 μg of calf thymus DNA (Sigma) as a carrier DNA and finally 1200 μl of 35% PEG4000 (which had been subjected to sterilized filtration). The mixture was then stirred sufficiently. A 750 μl portion of the stirred fluid was poured into a cuvette for Gene Pulser (BIORAD) and subjected once to an electric pulse treatment under the conditions of 1 μF and 1000 V. The cell suspension was transferred from the cuvette to a 15 ml tube and left standing at 30° C. for 1 hour. The cells were collected by centrifugation at 3,000 rpm for 5 minutes, suspended in 1 ml of a YPD medium and incubated at 30° C. for 4 hour. The cells were collected, suspended in 600 μl of sterilized water. A 150 μl of the suspension were spread onto YPD agar plates containing G418 (100 g/ml). The plates were incubated at 30° C. for 3 days to obtain the transformant SKB108.

The AATase activities of the transformant into which the AATase gene had been transfected and the control strains were measured. An SD liquid medium containing a leucine-free mixed amino acid solution (0.65% yeast nitrogen base (amino acid free; DIFCO), 2% glucose) was used for cultivating transformants of *Saccharomyces cerevisiae* TD4; an YPD liquid medium containing G418 (400 μg/ml) was used for cultivating transformants of sake yeast KYOKAI No. 9,; a YPD medium containing G418 (10 μg/ml) was used for cultivating transformants of brewery lager yeast AJL2155 strain. A 25 ml portion of the shaking culture product at 30° C. for about 16 hours was added to 1000 ml of the culture medium and the culture was incubated at 30° C. for 12 to 18 hours under static conditions.

The preparation of a crude enzyme and the assay of its activity were performed according to the procedures described in (1)-(ii) and (1)-(i). Protein concentration was determined with a BIORAD PROTEIN ASSAY KIT (BIORAD) according to the instructions of its manual.

The results for the *Saccharomyces cerevisiae* TD4, the sake yeast KYOKAI No. 9 and the beer yeast AJL 2155 are shown in Tables 4, 5 and 6, respectively. The results shows that the transformants of the present invention have AATase activities of 2 to 15 time higher than that of the untransformed stain. This indicates that the AATase gene according to the present invention facilely provides a strain which produces a large amount of an acetate ester such as isoamyl acetate.

TABLE 4

| Transformants | Crude enzyme activity (ppm/mg protein) |
| --- | --- |
| YEp13K/TD4 | 7.8 |
| YATK11/TD4 | 84.0 |
| YATL1/TD4 | 116.2 |
| YATL2/TD4 (SKB105) | 50.6 |

TABLE 5

| Transformants | Crude enzyme activity (ppm/mg protein) |
| --- | --- |
| K9 | 3.4 |
| YATK11G/K9 (SKB106) | 11.6 |

TABLE 6

| Transformants | Crude enzyme activity (ppm/mg protein) |
| --- | --- |
| AJL2155 | 4.1 |
| YATK11G/AJL2155 (SKB108) | 11.6 |

(8) Fermentation test of the transformants

Sake and beer were prepared by use of the yeast transformed with the AATase gene in the above (7).

(8)-(i) Production of sake with the transformant yeast

Small scale sake brewing test was carried out with 300 g rice according to the feed program as shown in Table 7. Thirty grams of malted rice (koji rice) and 110 ml of water including yeast ($2 \times 10^7$ cells/ml) (Koji rice) and lactic acid (0.35%(v/v)) were mixed and incubated at 15° C. On the second day, 35 g of steamed rice was added as the 1st feed. On the fourth day, the 2nd feed was carried out. After fermentation for 15 days, the fermentation product was centrifuged at 8,000 rpm for 30 minutes. Esters concentration of the "sake" liquor was measured. The results are shown in Table 8. The liquor produced by the transformant of the present invention has an aromatic flavor due to an enhanced amount of acetate esters such as ethyl acetate, isoamyl acetate in comparison with the liquor produced by yeast cells of KYOKAI-K9.

TABLE 7

| Feed program for small scale sake brewing | | | | |
| --- | --- | --- | --- | --- |
| | Seed Mash | 1st | 2nd | Total |
| Steamed rice | | 35 g | 213 g | 248 g |
| Koji rice | 30 g | | 22 g | 52 g |
| Water | 110 ml | | 310 ml | 420 ml |

TABLE 8

| Strain | EtOH (%) | NS | Ethyl acetate | ISo butanol | Isoamyl alcohol | Isoamyl acetate | Ethyl caproate |
| --- | --- | --- | --- | --- | --- | --- | --- |
| YKB106 | 18.3 | +12.1 | 38.8 | 88.7 | 211.0 | 7.5 | 0.6 |
| K-9 (Control) | 18.5 | +12.3 | 16.6 | 93.3 | 230.9 | 4.4 | 0.5 |

Unit: ppm
NS: Nippon Shudo (Sake degree)

(8)-(ii) Preparation of beer with transformant yeast

After yeast was added to the wort in which the original extract content was adjusted to 11° P, the mixture was incubated at 8° C. for 8 days, centrifuged at 3,000 rpm for 10 minutes and sterilized by filtration. Esters contained in the filtrated solution was measured. The results are shown in Table 9. The transformant of the present invention produced a liquor having an enhanced amount of acetate esters such as ethyl acetate, isoamyl acetate in comparison with the liquor produced by the untransformed yeast AJL2155.

TABLE 9

| Strain | Apparent extract content (°P) | Ethyl acetate (ppm) | Isoamyl acetate (ppm) | Isoamyl alcohol (ppm) |
| --- | --- | --- | --- | --- |
| SKB108 (YATL1G) | 2.3 | 22.8 | 0.99 | 51.2 |
| AJL2155 (Control) | 2.8 | 5.9 | 0.13 | 40.0 |

(9) Preparation of DNA encoding AATase from the wine yeast

Figure 5:
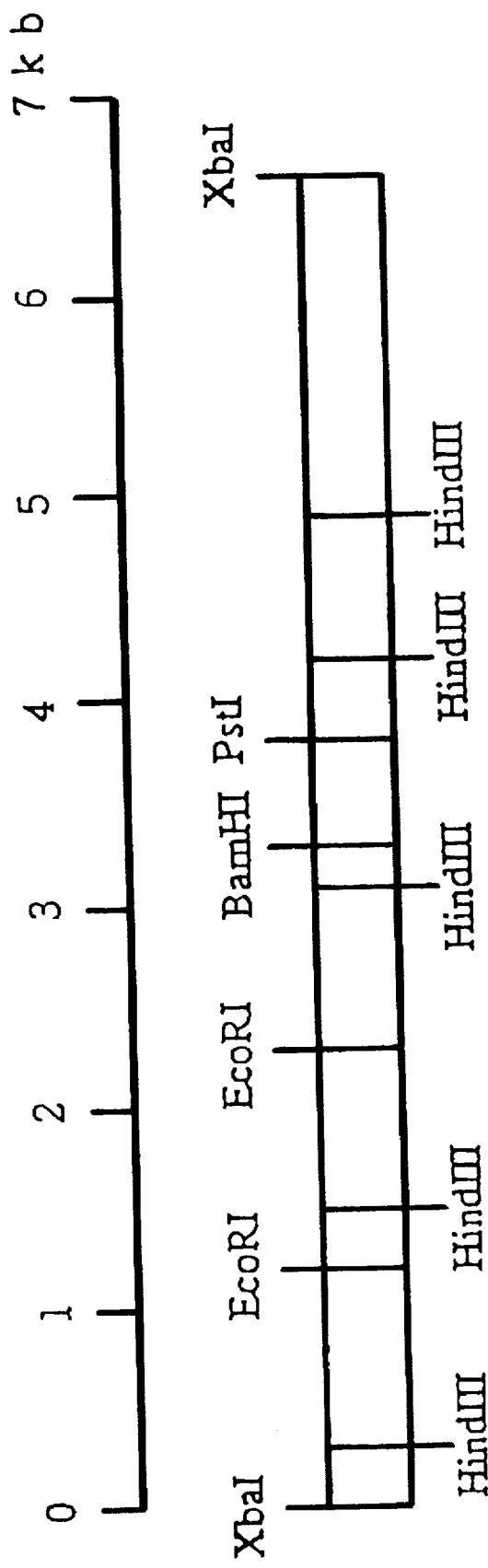
FIG. 5 shows a restriction map of the AATase originated from a wine yeast according to the present invention.

The primers A and B (SEQ ID NOS: 12 and 13, respectively) which have homology to two different sites in the sake yeast AATase gene shown in FIG. 6 were synthesized. Polymerase chain reaction (PCR) was performed with Gene Amp Reagent Kit (TAKARA SHUZO) and DNA Thermal Cycler (Parkin-Elmer-Theters Instruments Co.) using chromosomal DNA of wine yeast as a template with the two primers to give a 1.17 kb DNA fragment from the position of the primer A to the position of primer B. The process consisted of 30 cycles with annealing at 50° C. for 2 minutes. The reaction mixture was applied to agarose electrophoresis. The 1.17 kb DNA fragment was purified from the gel, labelled with 100 µCi [$^{32}$p ]dCTP using Nick Translation Kit (TAKARA SHUZO) and hybridized with 20,000 genome libraries of a wine yeast W-3 (YAMANASHI KOGYO GIJUTSU CENTER) prepared in the same manner as the sake yeast library. After the hybridization was carried out at 65° C., the membranes were rinsed with $2 \times$ SSC ($1 \times$ SSC is 15mM NaCl plus 1.5 mM sodium citrate) for 20 minutes, $2 \times$ SSC for 10 minutes and finally $0.1 \times$ SSC with gentle shaking at 65° C. As positive, 14 plaques were first obtained. Upon hybridizing these plaques with the 1.7 kb fragment in the same manner as the above, 7 positive plaques having a strong hybridization signal were obtained. The phage DNAs of these positive plaques were purified and subjected to restriction enzyme analysis. As a result, it was found that all of the 7 clones were of the same DNA having the restriction map shown in FIG. 5.

Deposition of the microorganisms

The microorganisms shown below related to the present invention have been deposited at Fermentation Research Institute of Agency of Industrial Science and Technology, Japan under the following deposition numbers under the Budapest Treaty on the international Recognition of the Deposit of Microorganisms for the Purpose of Patent Procedure.

| (1) SKB105 | FERM BP-3828 |
| --- | --- |
| (2) SKB106 | FERM BP-3829 |
| (3) SKB108 | FERM BP-3830 |

YATL2, YATK11G and YATL1G can be obtained by culturing SKB105, SKB106 and SKB108, respectively, under a certain condition, extracting therefrom the total DNA of the yeast (Methods in yeast genetics, Cold Spring Harbor Laboratory, 1988), transforming *Escherichia coli* with this total DNA and finally extracting the plasmids by the alkali method (lit: Molecular clonign, Cold Spring Harbor Laboratory, 1989).

A DNA fragment containing a part of the DNA sequence from A to B (bases 233-1808 of SEQ ID NO:14) of the DNA sequence shown in FIGS. 1 can be obtained by digesting YATK11G with an appropriate restriction enzyme. An example of a suitable DNA sequences is 1.6 kb HindIII fragment which is indicated by a double-headed arrow in FIG. 3.

What is claimed is:

1. An alcohol acetyltransferase (AATase) comprising a polypeptide selected from the group consisting of:

(a) a polypeptide having the amino acid sequence of SEQ ID NO:15, (b) a polypeptide having the amino acid sequence of SEQ ID NO:17, (c) a polypeptide having the amino acid sequence of SEQ ID NO:19 from amino acid residue 1 to amino acid residue 525, and (d) a polypeptide having the amino acid sequence of SEQ ID NO:19 from amino acid residue 19 to amino acid residue 525.

2. An AATase of claim 1, wherein said AATase is the polypeptide (a).

3. An AATase of claim 1, wherein said AATase is the polypeptide (b).

4. An AATase of claim 1, wherein said AATase is the polypeptide (c).

5. An AATase of claim 1, wherein said AATase is the polypeptide (d).

* * * * *